(12) United States Patent
Na et al.

(10) Patent No.: US 12,303,459 B2
(45) Date of Patent: May 20, 2025

(54) METHOD, SYSTEM, AND APPARATUS FOR DERMATOLOGICAL TREATMENT

(71) Applicants: SERENDIA LLC, San Juan Capistrano, CA (US); Jongju Na, San Juan Capistrano, CA (US)

(72) Inventors: Jongju Na, San Juan Capistrano, CA (US); Merle Richman, La Jolla, CA (US)

(73) Assignee: Serendia, LLC, Lake Forest, CA (US)

( * ) Notice: Subject to any disclaimer, the term of this patent is extended or adjusted under 35 U.S.C. 154(b) by 0 days.

(21) Appl. No.: 18/584,663

(22) Filed: Feb. 22, 2024

(65) Prior Publication Data

US 2024/0189183 A1    Jun. 13, 2024

Related U.S. Application Data

(63) Continuation of application No. 17/106,059, filed on Nov. 27, 2020, now abandoned, which is a
(Continued)

(30) Foreign Application Priority Data

| Aug. 8, 2008 | (KR) | ......................... 10-2008-0076993 |
| Feb. 3, 2015 | (KR) | ......................... 10-2015-0016793 |
| Aug. 13, 2015 | (KR) | ......................... 10-2015-0114641 |

(51) Int. Cl.
*A61N 1/05* (2006.01)
*A61H 15/02* (2006.01)
(Continued)

(52) U.S. Cl.
CPC .......... *A61H 39/086* (2013.01); *A61H 15/02* (2013.01); *A61H 39/002* (2013.01);
(Continued)

(58) Field of Classification Search
CPC .... A61H 39/086; A61H 39/007; A61H 15/02; A61H 2201/0153; A61H 2205/022;
(Continued)

(56) References Cited

U.S. PATENT DOCUMENTS

| 5,873,849 A | 2/1999 | Bernard |
| 5,993,269 A | 11/1999 | Ito |

(Continued)

FOREIGN PATENT DOCUMENTS

| JP | 60-002574 | 1/1985 |
| JP | 8-88040 | 4/1996 |

(Continued)

OTHER PUBLICATIONS

Na, J., Zheng, Z., Dannaker, C et al. Electromagnetic Initiation and Propagation of Bipolar Radiofrequency Tissue Reactions via Invasive Non-Insulated Microneedle Electrodes. Sci Rep 5, 16735 (2015).

(Continued)

*Primary Examiner* — Paula J Stice
(74) *Attorney, Agent, or Firm* — Danielson Legal LLC

(57) ABSTRACT

An apparatus for treating dermatological tissue, including at least two pins configured to be inserted in dermatological tissue to deliver electromagnetic energy to target dermatological tissue, and an electrical signal generator electrically coupled to the at least two pins, and creating a pulsed electrical signal across the at least two pins.

6 Claims, 21 Drawing Sheets

Related U.S. Application Data continuation-in-part of application No. 15/095,098, filed on Apr. 10, 2016, now abandoned, which is a continuation of application No. 14/598,208, filed on Jan. 15, 2015, now Pat. No. 9,630,002, which is a continuation of application No. 13/060,274, filed as application No. PCT/US2008/074131 on Aug. 22, 2008, now Pat. No. 8,979,912, said application No. 17/106,059 is a continuation-in-part of application No. 15/548,765, filed as application No. PCT/KR2016/001140 on Feb. 2, 2016, now abandoned.

(51) Int. Cl.

| | |
|---|---|
| A61H 39/00 | (2006.01) |
| A61H 39/08 | (2006.01) |
| A61M 37/00 | (2006.01) |
| A61N 1/32 | (2006.01) |
| A61N 1/36 | (2006.01) |
| A61N 5/06 | (2006.01) |
| A61B 17/34 | (2006.01) |
| A61H 15/00 | (2006.01) |
| A61H 23/02 | (2006.01) |

(52) U.S. Cl.
CPC ........... *A61H 39/007* (2013.01); *A61M 37/00* (2013.01); *A61N 1/0502* (2013.01); *A61N 1/328* (2013.01); *A61N 1/36017* (2013.01); *A61N 5/0616* (2013.01); *A61N 5/062* (2013.01); *A61N 5/0624* (2013.01); *A61B 2017/3409* (2013.01); *A61H 2015/0014* (2013.01); *A61H 23/02* (2013.01); *A61H 2039/005* (2013.01); *A61H 2201/0153* (2013.01); *A61H 2201/105* (2013.01); *A61H 2201/1207* (2013.01); *A61H 2201/1604* (2013.01); *A61H 2201/169* (2013.01); *A61H 2201/5007* (2013.01); *A61H 2201/5097* (2013.01); *A61H 2205/022* (2013.01); *A61H 2205/04* (2013.01); *A61H 2205/06* (2013.01); *A61H 2205/065* (2013.01); *A61H 2205/084* (2013.01); *A61H 2205/10* (2013.01); *A61H 2205/12* (2013.01); *A61M 2037/0007* (2013.01); *A61M 2037/0023* (2013.01); *A61M 2205/8206* (2013.01); *A61N 2005/0644* (2013.01); *A61N 2005/0652* (2013.01); *A61N 2005/0659* (2013.01); *A61N 2005/0661* (2013.01)

(58) Field of Classification Search
CPC .. A61N 5/062; A61N 1/36017; A61N 1/0502; A61N 1/328; A61N 2005/0659; A61N 2005/0661; A61N 2005/0644; A61N 2005/0652; A61N 1/0504; A61N 1/18; A61N 5/0616; A61N 5/0619; A61N 5/0625

See application file for complete search history.

(56) References Cited

U.S. PATENT DOCUMENTS

| | | | |
|---|---|---|---|
| 6,391,005 | B1 | 5/2002 | Lum et al. |
| 6,523,420 | B2 | 2/2003 | Lee et al. |
| 7,220,134 | B2 | 5/2007 | Goodman et al. |
| 7,347,860 | B2 | 3/2008 | Ouchi |
| 7,824,394 | B2 | 11/2010 | Manstein |
| 8,666,487 | B2 | 3/2014 | Kang |
| 9,320,536 | B2 | 4/2016 | Na |
| 9,480,836 | B2 | 11/2016 | Na |
| 2001/0021868 | A1 | 9/2001 | Herbst et al. |
| 2002/0128641 | A1* | 9/2002 | Underwood ........... A61B 18/14 606/41 |
| 2004/0198241 | A1 | 10/2004 | Crawford et al. |
| 2005/0171534 | A1 | 8/2005 | Habib |
| 2005/0222565 | A1 | 10/2005 | Manstein |
| 2007/0066094 | A1 | 3/2007 | Kim et al. |
| 2008/0082090 | A1* | 4/2008 | Manstein ............. A61B 18/203 606/9 |
| 2008/0197869 | A1 | 8/2008 | Miyagi et al. |
| 2010/0217254 | A1 | 8/2010 | Mehta |

FOREIGN PATENT DOCUMENTS

| | | |
|---|---|---|
| JP | 9-215806 | 8/1997 |
| JP | 2543161 | 8/1997 |
| JP | 10-189087 | 7/1998 |
| JP | 11-307161 | 11/1999 |
| JP | 2000-39449 | 2/2000 |
| JP | 2000-299154 | 10/2000 |
| JP | 2001-522274 | 11/2001 |
| JP | 2002-117926 | 4/2002 |
| JP | 2005-351785 | 12/2005 |
| JP | 2007-014488 | 1/2007 |
| JP | 2007-507247 | 3/2007 |
| JP | 2007-110104 | 4/2007 |
| JP | 4406706 | 11/2009 |
| JP | 4441227 | 1/2010 |
| JP | 5065005 | 10/2012 |
| JP | 5908977 | 4/2016 |
| KR | 20-0172727 | 3/2000 |
| KR | 20-0176242 | 4/2000 |
| KR | 10-0264548 | 9/2000 |
| KR | 20-0201331 | 12/2000 |
| KR | 10-0308121 | 11/2001 |
| KR | 10-0310340 | 11/2001 |
| KR | 20-0268667 | 3/2002 |
| KR | 20-0284460 | 8/2002 |
| KR | 10-0428782 | 4/2004 |
| KR | 10-0503628 | 7/2005 |
| KR | 10-0555713 | 3/2006 |
| KR | 20-0410268 | 3/2006 |
| KR | 10-2006-0061011 | 6/2006 |
| KR | 10-2006-0061012 | 6/2006 |
| KR | 10-2008-0077326 | 8/2008 |
| KR | 10-2009-0067572 | 6/2009 |
| KR | 10-0943089 | 2/2010 |
| KR | 10-2011-0002210 | 1/2011 |
| KR | 10-2012-0090007 | 8/2012 |
| KR | 10-1181870 | 9/2012 |
| KR | 10-1363000 | 2/2014 |

OTHER PUBLICATIONS

Intracel - Fractional RF technology, Youtube, uploaded by CMedTechnologies, Apr. 8, 2011 https://www.youtube.com/ watch?v=7liHVfsgh60.

Un-Cheol Yeo, "Evaluation of the wound healing response post deep dermal heating by fractional RF: INTRAcel", 12th Symposium of the Association of Korean Dermatologist, 2009.

Matthias Zenker, Argon Plasma Coagulation, GMS Krankenhaushygiene Interdisziplinär 2008, vol. 3(1), ISSN 1863-5245.

Dany Berube, et al., "A Predictive Model of Minimally Invasive Bipolar Fractional Radiofrequency Skin Treatment", Lasers in Surgery and Medicine 41:473-478 (2009).

Sang Ju Lee, et al., "Use of Fractionated Microneedle Radiofrequency for the Treatment of Inflammatory Acne Vulgaris in 18 Korean Patients", Mar. 2012.

Webster, J. G. (1992). Macroshock Hazards. In Medical instrumentation: Application and design. essay, Houghton Mifflin. page 634 (Year: 1992).

Fish RM, Geddes LA. Conduction of electrical current to and through the human body: a review. Eplasty. Oct. 1, 20092;9:e44. PMID: 19907637; Pmcid: PMC2763825. (Year: 2009).

\* cited by examiner

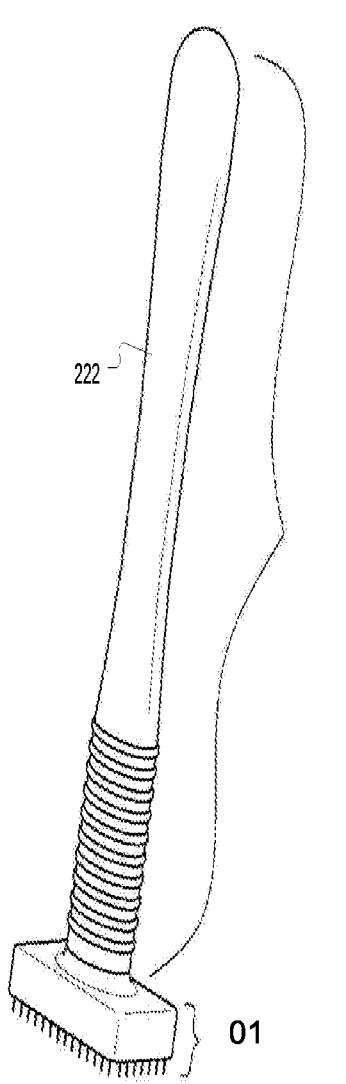
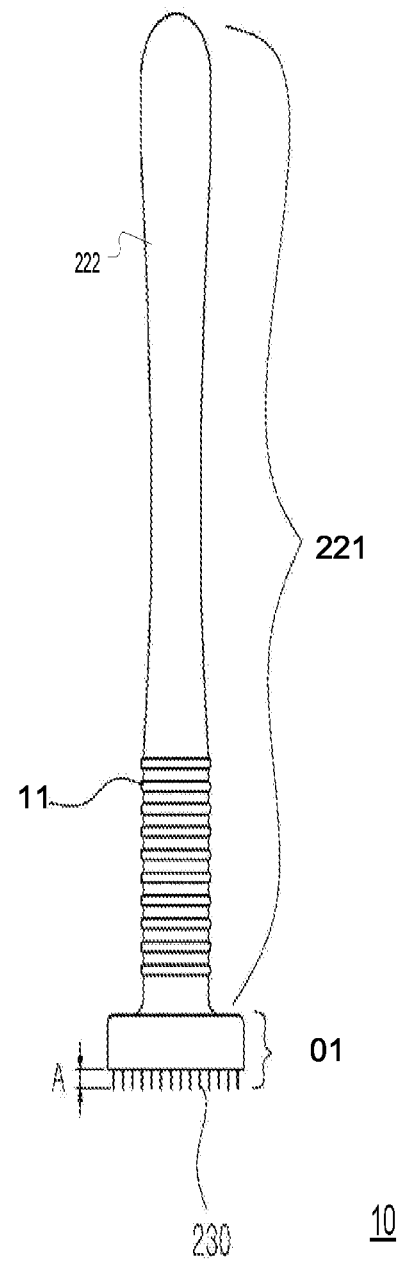
FIGURE 1A                    FIGURE 1B

ized Patent Application No. 10-2008-0076993, filed on Aug. 8, 2008,
METHOD, SYSTEM, AND APPARATUS FOR DERMATOLOGICAL TREATMENT

CROSS-REFERENCE TO RELATED APPLICATIONS

This is a continuation application of U.S. patent application Ser. No. 17/106,059 filed on Nov. 27, 2020 (now pending), the disclosure of which is incorporated herein by reference in its entirety. U.S. patent application Ser. No. 17/106,059 is a continuation-in-part of U.S. application Ser. No. 15/095,098, filed on Apr. 10, 2016, which is a continuation of U.S. application Ser. No. 14/598,208, filed on Jan. 15, 2015, now issued as U.S. Pat. No. 9,630,002, which is a continuation of U.S. application Ser. No. 13/060,274, filed on Mar. 20, 2011, now issued as U.S. Pat. No. 8,979,912, which is the National Stage entry of PCT Application No. PCT/US2008/074131, filed on Aug. 22, 2008, and which claims priority from and the benefit of Korean Patent Application No. 10-2008-0076993, filed on Aug. 8, 2008, which are all hereby incorporated by reference for all purposes as if fully set forth herein. U.S. patent application Ser. No. 17/106,059 is a continuation-in-part of U.S. application Ser. No. 15/548,765, filed on Aug. 3, 2017, which is the National Stage entry of PCT Application No. PCT/KR2016/001140, filed on Feb. 2, 2016, and which claims priority from and the benefit of Korean Patent Application Nos. 10-2015-0114641, filed on Aug. 13, 2015 and 10-2015-0016793, filed on Feb. 3, 2015, which are all hereby incorporated by reference for all purposes as if fully set forth herein.

BACKGROUND

Field

Various embodiments described herein relate generally to treating dermatological tissue, including systems, and methods used in treating dermatological tissue. Various embodiments also relate to a method and system for treating vessels of skin or vessels associated with skin appendage in skin via electric signals. More particularly, to treating blood vessels via electric signals.

Discussion of the Background

It may be desirable to treat dermatological tissue, the present invention provides such treatment.

While sun exposure, pregnancy, medications, hormonal changes in the body, and genetic factors are thought to affect the development of melasma, dermal melasma, hyperpigmentation, hypopigmentation, rosacea, flushing, erythema, and telangiectasia, the exact mechanisms thereof have yet to be clarified.

Meanwhile, although treatments for hair loss, hair removal, excessive sebaceous gland secretion, excessive sweating, and axillary osmidrosis are increasing in popularity, their efficacy is limited. Research and development of treatment that provide better therapeutic results is warranted.

Some conventional skin treatments employing light energy, LASER energy, and multi-wavelength light energy therapy such as intensive pulsed light (IPL), are not only ineffective at treating targeted vessel at deeper portions of skin, but they also pose an increased risk of damaging skin due to excessive heating thereof during treatment.

Of these conventional therapies, IPL is commonly associated with overheating/burning skin, which may lead to post-inflammatory hyperpigmentation (PIH), as shown in FIG. 9.

The above information disclosed in this Background section is only for enhancement of understanding of the background of the inventive concept, and, therefore, it may contain information that does not form the prior art that is already known in this country to a person of ordinary skill in the art.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

FIG. 1A is a simplified isometric diagram of a dermatological treatment apparatus according to various embodiments.

FIG. 1B is a simplified, side diagram of the dermatological treatment apparatus according to various embodiments.

DETAILED DESCRIPTION OF THE ILLUSTRATED EMBODIMENTS

Figure 1C:
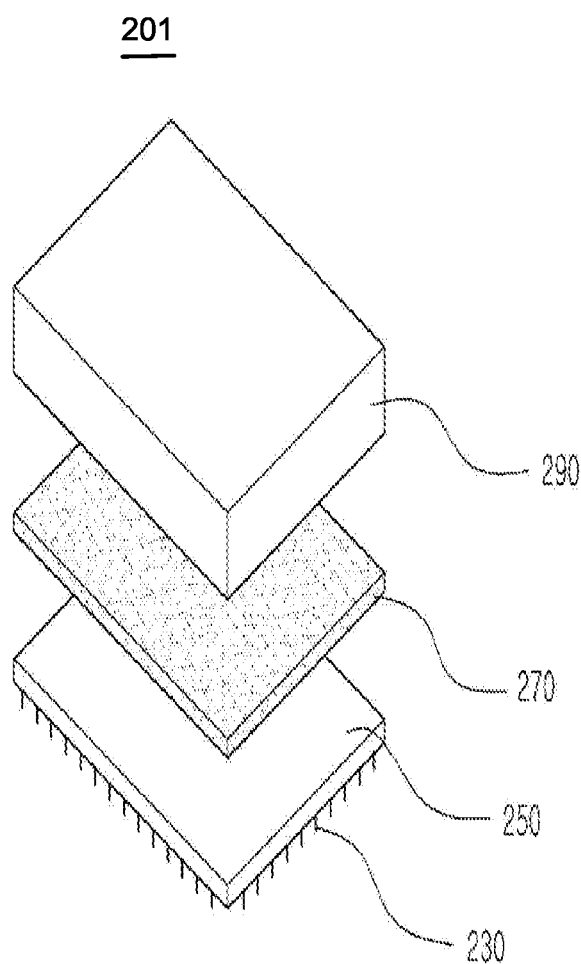
FIG. 1C is a simplified, exploded view of layers of the dermatological treatment apparatus according to various embodiments.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

FIG. 1A is a simplified isometric diagram and FIG. 1B is a simplified side view of a dermatological treatment apparatus 10 according to various embodiments. The apparatus 10 may include a user handle 221 coupled to an acupuncture plate 201. In an embodiment the plate 201 may be elastically coupled to the handle segment 222 via an elastomeric section 211. The elastomeric section may be comprised of a combination of elastomeric materials and non-elastomeric materials. The elastomeric materials may include plastics, rubber (synthetic or natural), and spring(s).

FIG. 1C includes a simplified exploded view of an embodiment of an acupuncture plate 201 according to various embodiments. The plate 201 may include an upper, substantially rigid section or layer 290, deformable or elastic section 270 or layer, and acupuncture section or layer 250.

Figure 1D:
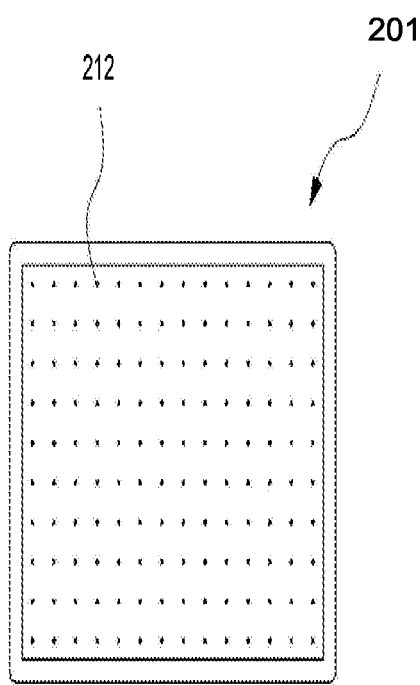
FIG. 1D is a simplified view of a layer of a dermatological treatment apparatus according to various embodiments.

The acupuncture section 250 may include a plurality of acupuncture pins or needles 230. FIG. 1D is a simplified bottom view of the plate 201 showing the location or holes 212 for the pins or needles 230. In an embodiment the plate 201 may have a rectangular cross section having a dimensional about 1 to 4 cm in width and about 1 to 6 cm in length. The plate 201 may any shape including circular, elliptical, polygon, or other shape where the shape may be particular to a dermatological area to be treated.

In an embodiment the plate may include about 140 pins or needles 230 uniformly separated. Each needle may be about 0.1 to 0.4 mm in diameter and 0.2 mm to 1.4 mm in length including 0.3 mm in diameter and 0.8 mm in length in an embodiment. The elastic section or layer 270 may be comprised of a combination of elastomeric materials and non-elastomeric materials. The elastomeric materials may include plastics, rubber (synthetic or natural), and spring(s). The pin section 230 may be coupled directly or indirectly to the upper section 290 via the elastic section 250, including via glues, screws, welds, or other connection. In an embodiment the pin section 250 may include elastomers to enable at least partial deformation of the pin section 250 about the pins 230.

In operation a user may employ the apparatus 10 to create a plurality of micro-wounds or holes in dermatological layers of a mammal's 20 skin or dermis. The micro-wound or hole creation may improve the absorption or application of one or more chemicals applied on or about the micro-wounds or holes.

Figure 2A:
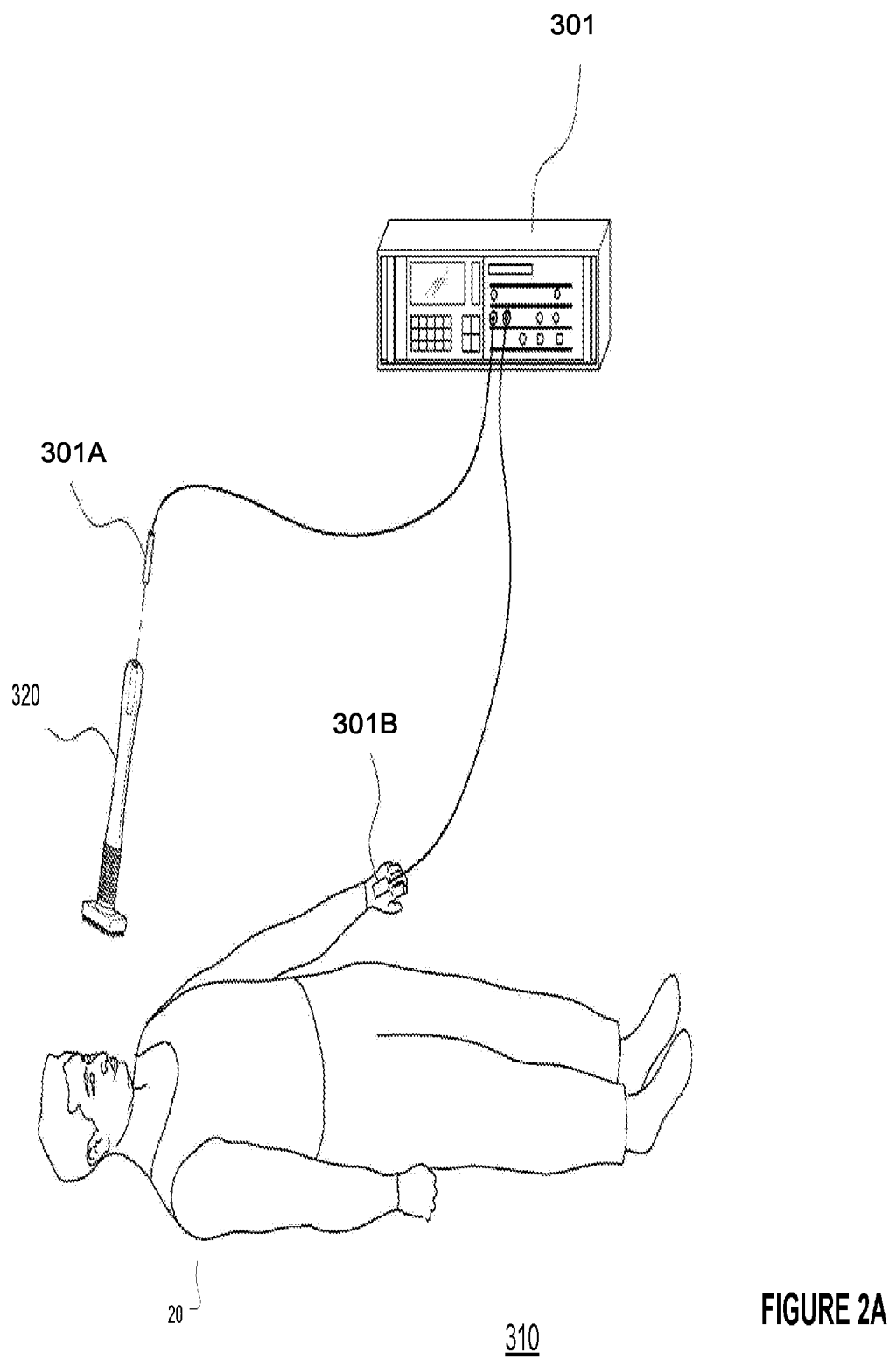
FIG. 2A is a simplified isometric diagram of a dermatological treatment architecture according to various embodiments.
Figure 2B:
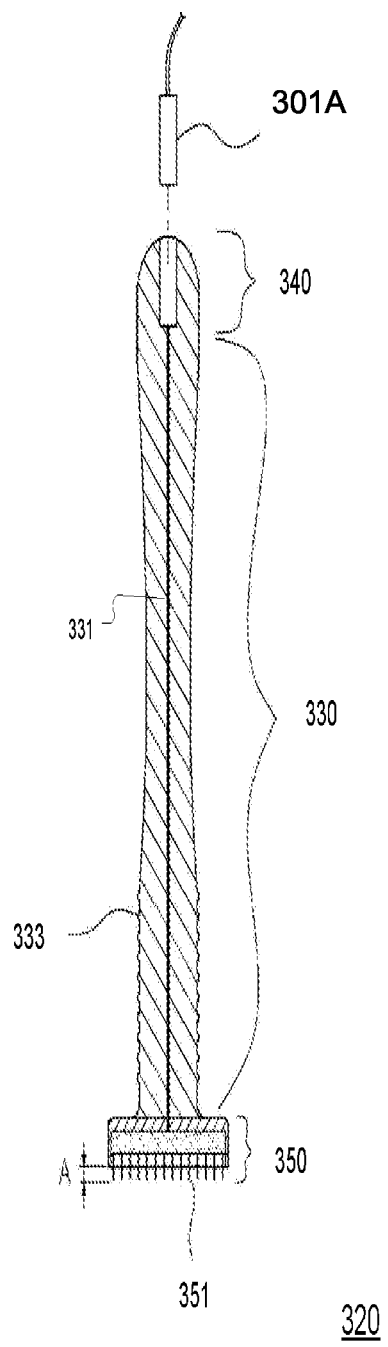
FIG. 2B is a simplified cross-sectional diagram of a dermatological treatment apparatus according to various embodiments.

FIG. 2A is a simplified diagram of a dermatological treatment architecture 310 according to various embodiments. Architecture 310 includes an acupuncture apparatus 320 and an electrical signal generation system 301. The electrical signal generation system 301 may be electrically coupled to the acupuncture apparatus 320 via one or more wires 301A and to a mammal 20 to be treated via one or more wires 301B. FIG. 2B is a simplified cross-sectional diagram of the acupuncture apparatus 320 according to various embodiments. The apparatus 320 may include a handle 330, elastic section 333, electrical interface 340, internal wire(s) 331 and plate 350. The pins 351 may have a length A (0.3 mm to 2.1 mm in an embodiment) where at least one pin 351 is electrically coupled to the electrical interface 340 via the internal wire 331. The electrical interface 340 may be removably connected to the system 301 wire 301A.

Figure 2C:
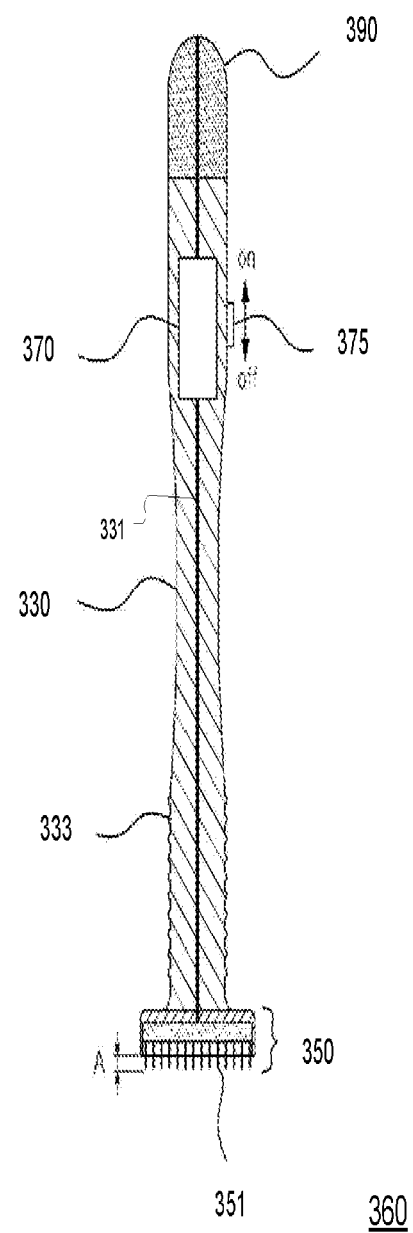
FIG. 2C is a simplified cross-sectional diagram of another dermatological treatment apparatus according to various embodiments.
Figure 5B:
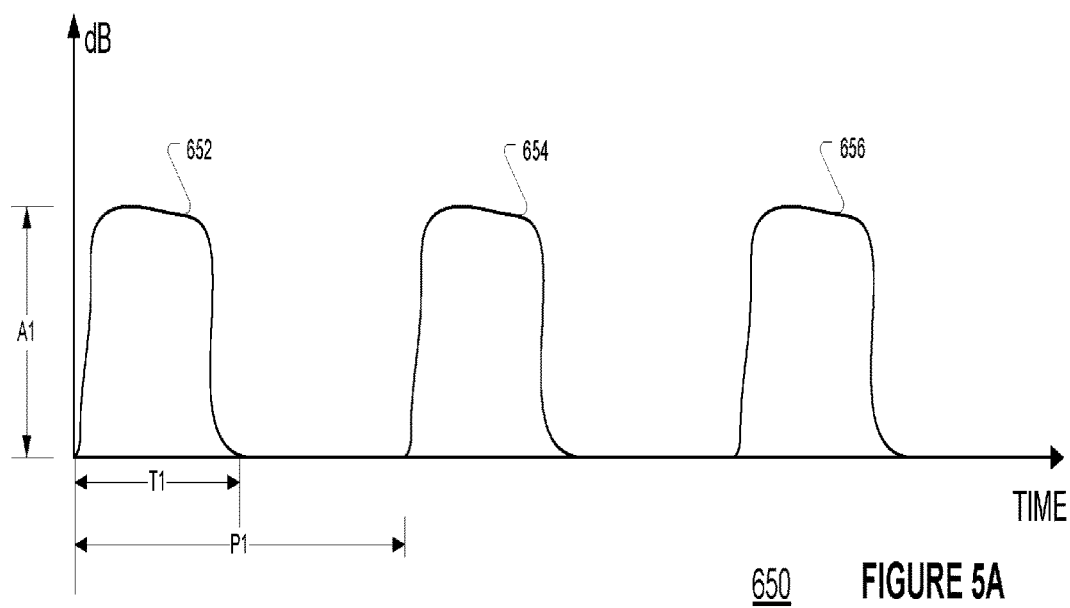
FIG. 5A-6 are diagrams of signals that may be applied to one or more dermatological treatment systems according to various embodiments.
Figure 5B:
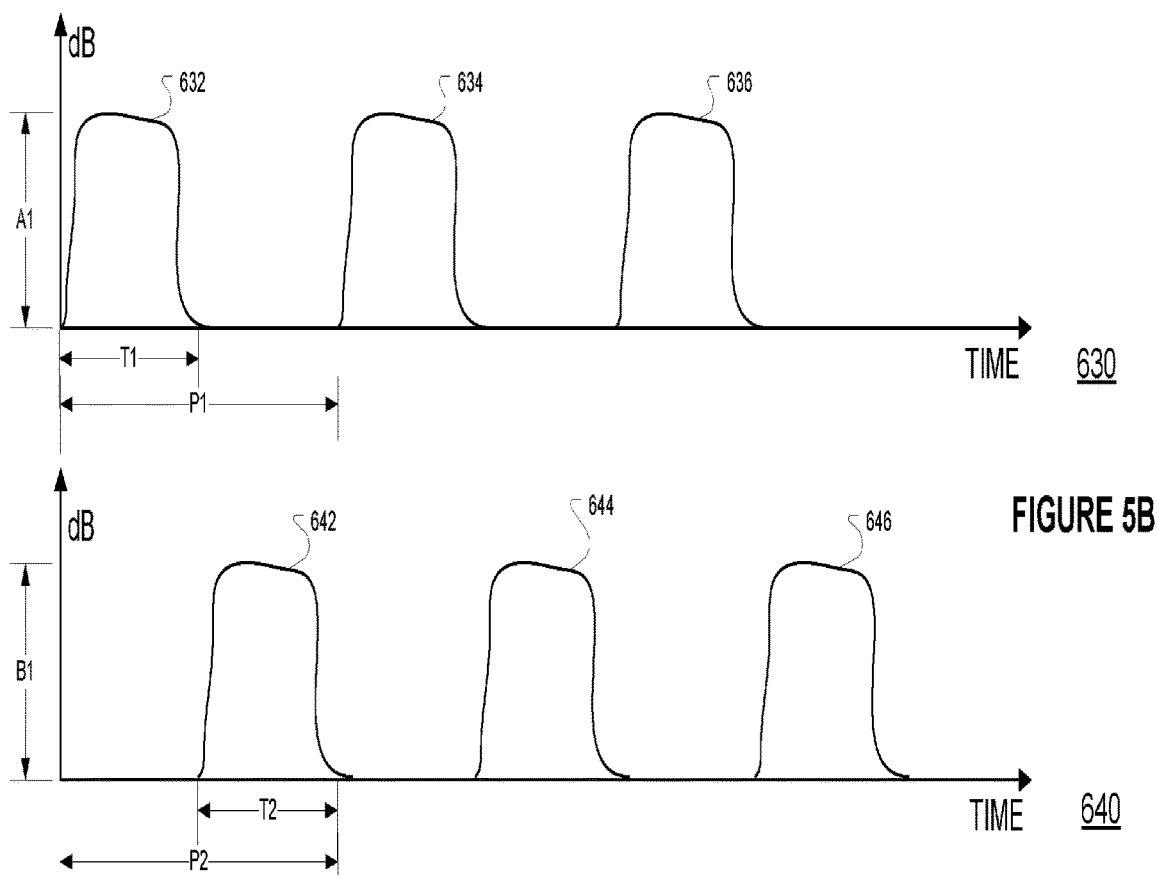
Figure 6:
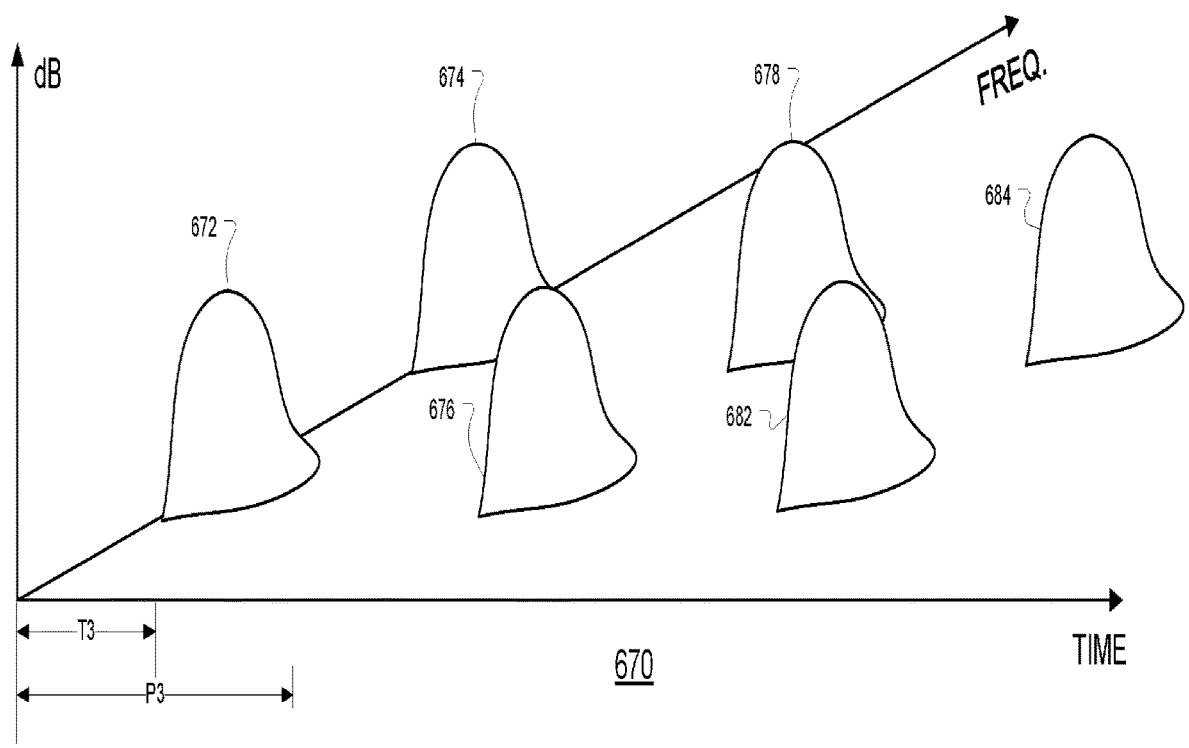

The electrical signal generation system 301 may generate a variety of signals (such as shown in FIGS. 5A to 6) to vibrate one or more pins 351 electrically coupled to the system 301 via the internal wire 331 and lead 301A. A pin vibration 351 may increase the micro-wound or cut formed in dermis by the pin 351. FIG. 2C is a simplified cross-sectional diagram of an acupuncture apparatus 360 according to various embodiments. The apparatus 360 may include a handle 330, an elastic section 333, an electrical conductive interface 390, internal wire(s) 331, signal generator 370, switch 375, and plate 350. The signal generator 370 may be coupled to at least one pin 351 via internal wire 331 and coupled to the conductive interface 390.

The signal generator or module 370 may generate a variety of signals (such as shown in FIGS. 5A to 6) to vibrate one or more pins 351 electrically coupled to the system 301 via the internal wire 331 and the conductive interface 390. In operation a user 20 may touch the conductive interface 390 and place one or more electrically coupled pins 351 in contact with their dermis to form an electrical pathway from the pin 351 to the electrical conductive interface 390. The signal generator 370 may include a battery to supply energy to generate one or more electrical signals. The switch 375 coupled to the generator 370 may cause the generator to produce one or more electrical signals for a predetermined time interval or until the switch 375 is triggered again. As noted a pin vibration 351 may increase the micro-wound or cut formed in dermis by the pin 351.

Figure 2D:
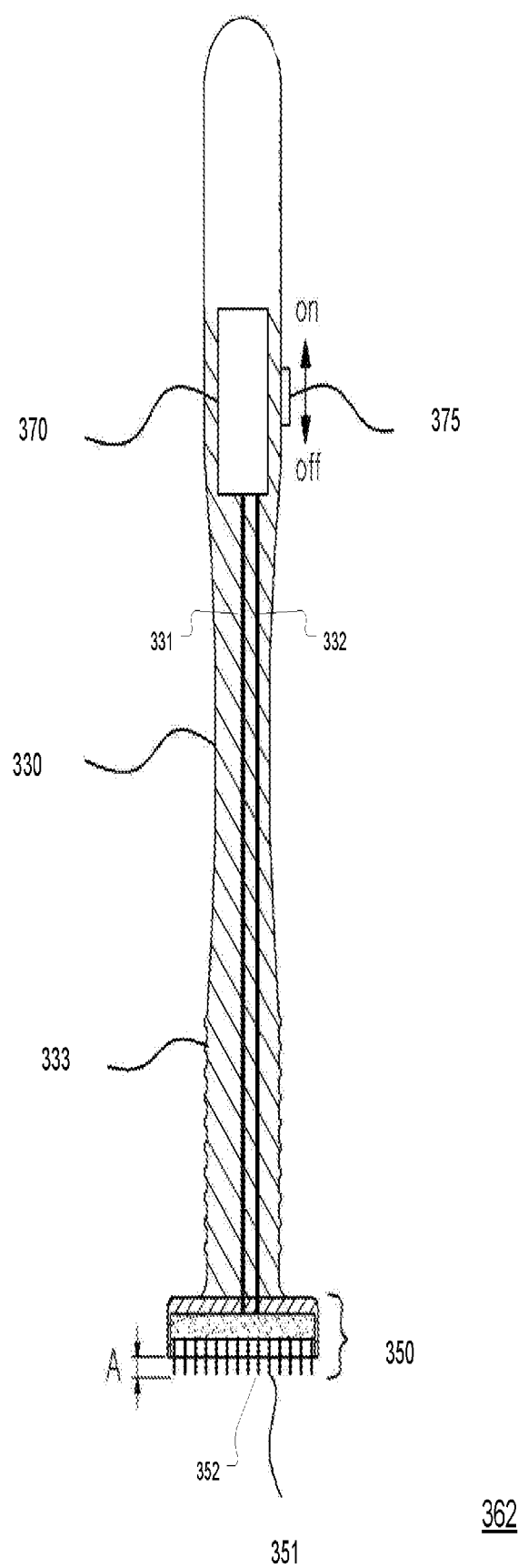
FIG. 2D is a simplified cross-sectional diagram of another dermatological treatment apparatus according to various embodiments.

FIG. 2D is a simplified cross-sectional diagram of an acupuncture apparatus 362 according to various embodiments. The apparatus 362 may include a handle 330, an elastic section 333, internal wire(s) 331, 332, signal generator 370, switch 375, and plate 350. The signal generator 370 may be coupled to at least one pin 351 via internal wire 331 and coupled to at least one other pin 352 via internal wire 332. When active the pins 351, 352 may form at least one dipole pair. The signal generator or module 370 may generate a variety of signals (such as shown in FIGS. 5A to 6) to vibrate one or more dipole pair or bipolar pins 351, 352.

Figure 2E:
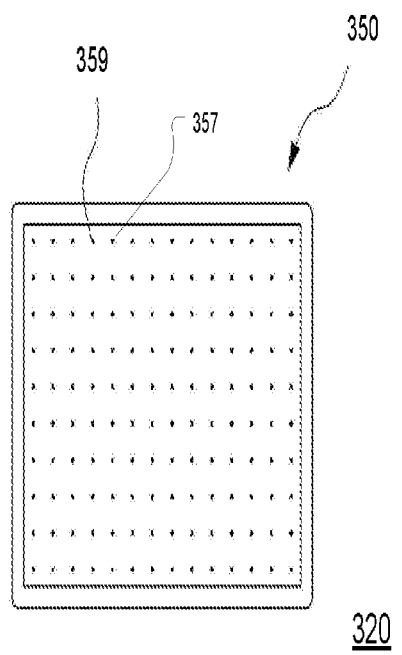
FIG. 2E is a simplified view of a layer of a dermatological treatment apparatus according to various embodiments.
Figure 2F:
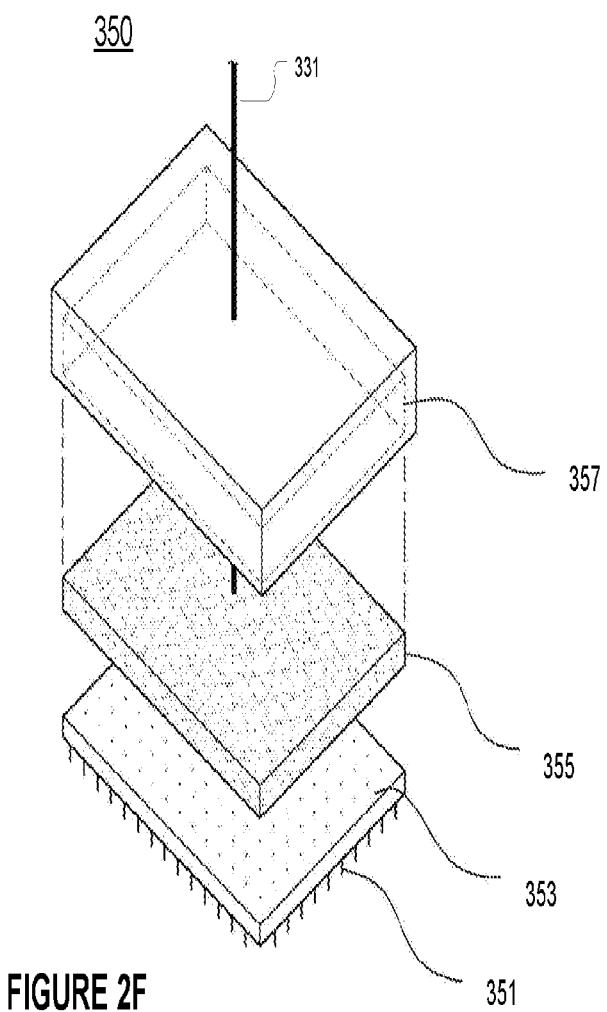
FIG. 2F is a simplified, exploded view of layers of the dermatological treatment apparatus according to various embodiments.

FIG. 2F includes a simplified exploded view of an embodiment of an acupuncture plate 350 including at least one electrically coupled pin 351 according to various embodiments. The plate 350 may include an upper, substantially rigid section or layer 357, deformable or elastic section 355 or layer, and acupuncture section or layer 353. The acupuncture section 353 may include a plurality of acupuncture pins or needles 351 where at least one pin 351 is electrically coupled to the wire 331. In a bipolar configuration a second wire 332 may be coupled to at least one other pin 351. FIG. 2E is a simplified bottom view of the plate 350 showing the pins or needles 359, 357 where the pins may be electrically coupled to a first wire 331 and a second wire 332 to form dipole pair (bipolar pins).

In an embodiment the plate 350 may have a rectangular cross section having a dimensional about 1 to 4 cm in width and about 1 to 6 cm in length. The plate 350 may any shape including circular, elliptical, polygon, or other shape where the shape may be particular to a dermatological area to be treated.

In an embodiment the plate may include about 140 pins or needles 351 uniformly separated. Each needle may be about 0.1 to 0.4 mm in diameter and 0.2 mm to 1.4 mm in length including 0.3 mm in diameter and 0.8 mm in length in an embodiment. The elastic section or layer 355 may be comprised of a combination of elastomeric materials and non-elastomeric materials. The elastomeric materials may include plastics, rubber (synthetic or natural), and spring(s). The pin section 353 may be coupled directly or indirectly to the upper section 357 via the elastic section 353, including via glues, screws, welds, or other connection. In an embodiment the pin section 353 may include elastomers to enable at least partial deformation of the pin section 353 about the pins 351.

Figure 3A:
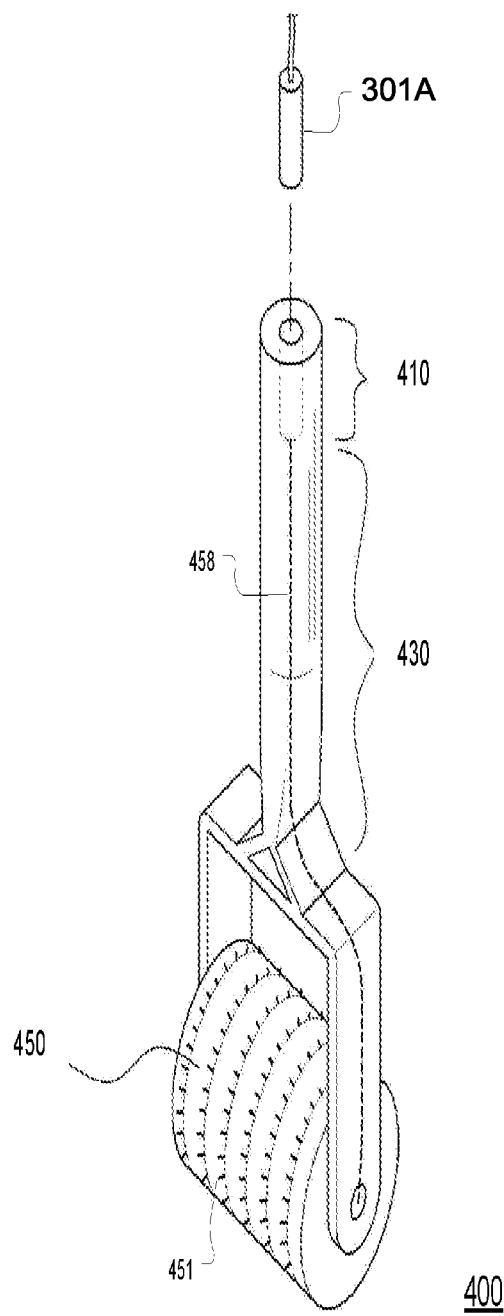
FIG. 3A is a simplified isometric diagram of a dermatological treatment apparatus according to various embodiments.
Figure 3B:
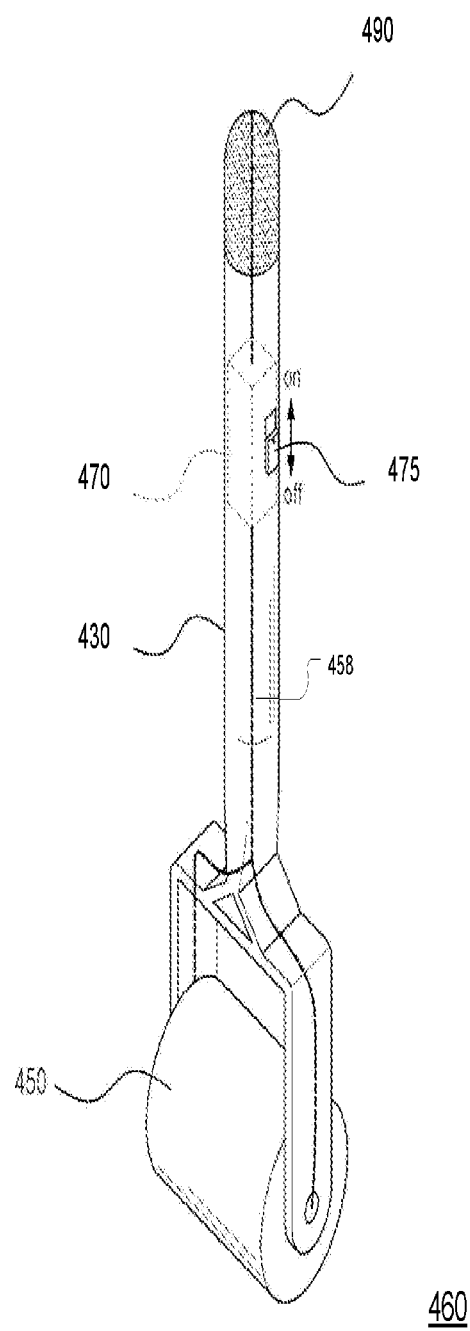
FIG. 3B is a simplified isometric diagram of another dermatological treatment apparatus according to various embodiments.

FIGS. 3A and 3B are simplified isometric diagrams of acupuncture apparatus 400, 460 including at least one pin 451 that may be coupled to an electrical signal via an internal wire 458. Each apparatus 400, 460 includes curved roller 450 having a plurality of acupuncture pins 451 where the pins 451 may be similar to pins 351. In apparatus 400, the electrical lead wire 400A may be coupled to an electrical interface 410 in the apparatus handle 430 where the interface 410 is electrically coupled to the internal wire 458. In apparatus 460, the handle 430 may include a signal generator 470 similar to generator 370, switch 475, and conduction surface 490. Apparatus 460 may operate similar to apparatus 360 in operation other than the rolling capability of the apparatus 460, 400. In an embodiment the rollers 450 may have various configurations to conform to a dermal area to be treated.

Figures 4A, 4B:
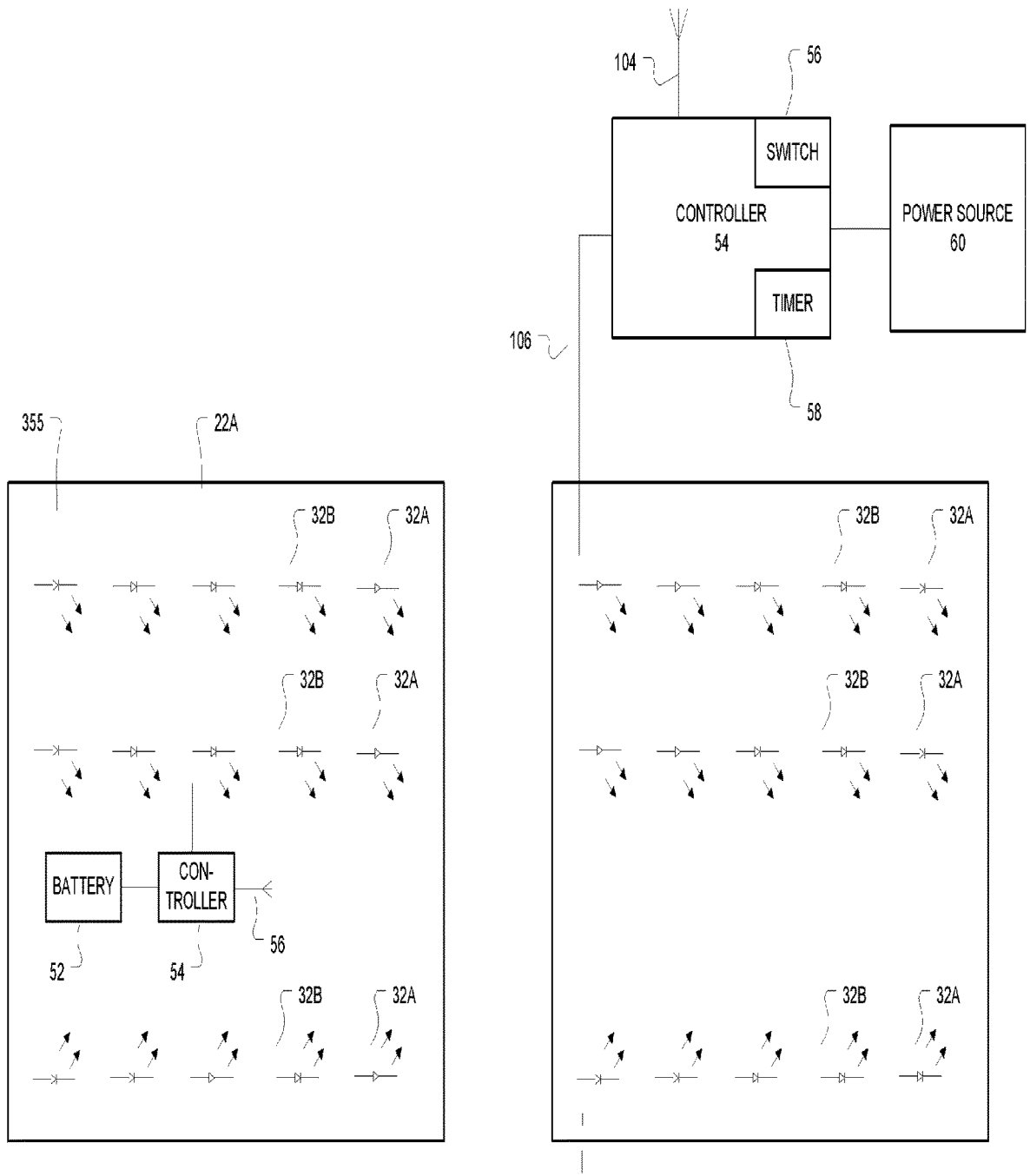
FIG. 4A is a simplified view of a layer of a dermatological treatment apparatus according to various embodiments.
FIG. 4B is a simplified view of a layer and apparatus of a dermatological treatment system according to various embodiments.
Figure 4C:
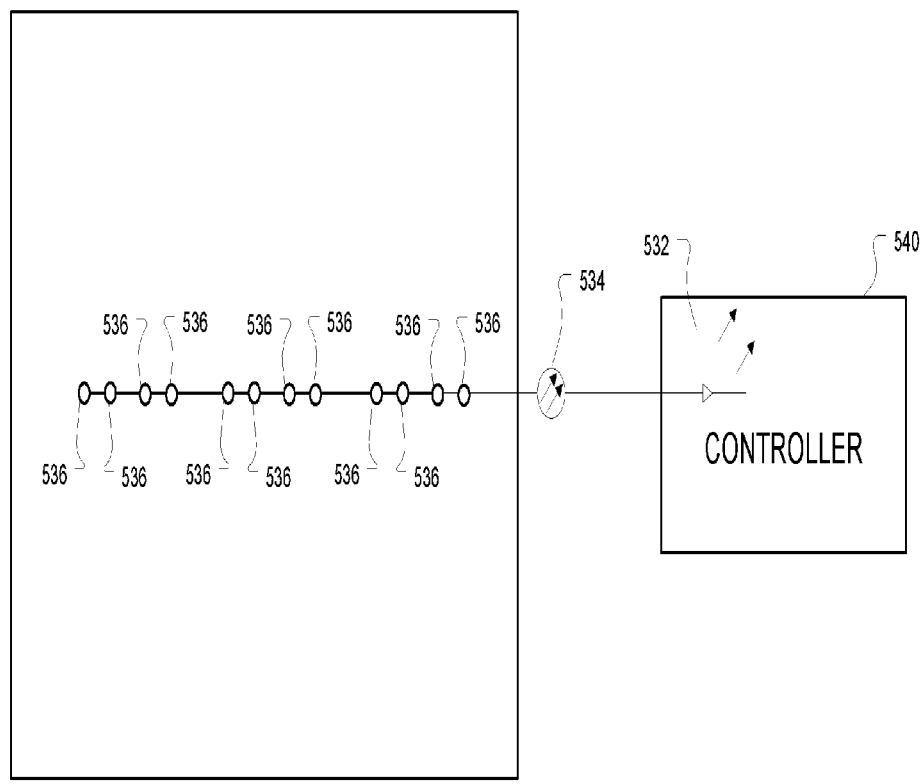
FIG. 4C is a simplified view of a layer and apparatus of a dermatological treatment system according to various embodiments.

In any of the above apparatus 10, 320, 350, 360, 400, 460, the plate or roller 201, 350, 450 may include a plurality of embedded LEDs 32A, 32B, a battery 52, a controller 54, and an antenna 56 as shown in FIG. 4A. In an embodiment the LED 32A may be configured to emit energy of a first particular frequency range and the LED 32B may be configured to emit energy of a second particular frequency range. The surface 22 of a roller 450, plate 201, 350, 450 may also be embedded with a chemical 22A that may be used to treat dermatological cells. The chemical 22A may be reactive to the first and the second frequency ranges. Further dermatological cells may be reactive to the first and the second frequency ranges. In addition, the combination of the chemical 22A and the application of the first and the second frequency ranges to the chemical 22A and dermatological cells may have a synergetic effect.

In an embodiment the chemical 22A may be applied directly to the dermatological cells to be treated. In a further embodiment a chemical 22A may not be employed in addition to the apparatus 10, 320, 350, 360, 400, 460. In an embodiment the pin section 250, 353, may be translucent and comprised of a polyurethane, medical silicon, or other pliable, translucent, hypoallergenic material.

In an embodiment the local controller 54 and battery 52 may also be embedded in the upper section 290, 357, pin section 230, 351, or the handle 221, 330, or separately between these sections. The controller 54 may be electrically coupled to the one or more LEDS 32A, 32B. The controller 54 may also be coupled to a battery 52. The controller 54 may generate one or more signals for LEDs 32A, 32B as a function of a user switch 75, 56. The signals may vary as a function of the first and second frequency ranges. The controller 54 may include one or more timers 58 that may limit the application of energy to the LEDs 32A, 32B to predetermined time intervals. In an embodiment the controller may also be coupled to an antenna 56 to receive or transmit one or more signals related to the transmission of energy to one or more LEDs 32A, 32B. In an embodiment the system 30 may be configured to treat a particular segment of dermatological cells such as a face. The apparatus 10 may be configured to conform to a user's anatomy so that emitted light is focused on dermatological cells. In another embodiment, the system 201 may be configured to treat another anatomical region including dermatological cells on an arm, leg, chest, hands, feet, neck, or other region.

In an embodiment 510 shown in FIG. 4B, a controller 54, an antenna 104, and a power source 60 may be located in external to the apparatus 10, 320, 360. The power source 60 may be coupled to the controller 54. The controller 54 may be coupled to one or more LEDs 32A, 32B via one or more electric wires 106. The controller 54 may generate one or more signals for LEDs 32A, 32B as a function of the user switch 56. The signals may vary as a function of the first and second frequency ranges. The controller 54 may include one or more timers 58 that may limit the application of energy to the LEDs 32A, 32B to predetermined time intervals. In an embodiment the controller may also be coupled to an antenna 104 to receive or transmit one or more signals related to the transmission of energy to one or more LEDs 32A, 32B.

In any of the above apparatus 10, 320, 350, 360, 400, 460, the plate or roller 201, 350, 450 may include a plurality of embedded LED lens 536, a fiber optic pathway 534, and an LED 532. In this embodiment the LED 532 may be coupled to lens 536 via the fiber optic pathway 534. The controller 540 may generate an LED signal via the LED 532 that is transmitted to dermatological cells via the lens 536 and the fiber optic pathway 534.

FIGS. 5A-5B are diagrams of electrical signal waveforms 650, 630, 640 that may be applied to one or more LEDs 32A, 32B, 532 and to the pins 230,351,451 according to various embodiments. The signal waveform 650 includes several square-wave pulses 652, 654, 656 that may be applied to an LED 32A, 32B, 532. Each pulse 652, 654, 656 may a have a similar magnitude and envelope. The waveform 650 may be used to energize an LED 32A, 32B, 532 and to the pins 230,351,451 periodically P1 for a predetermined interval T1 where each pulse 652, 654, 656 has a amplitude A1. In an embodiment, A1 may be about 0.1 milliamperes (mA) to 10 mA, the pulse width T1 may be about 100 microsecond (μs) to 500 μsand the period P1 may from 100 ms to 500 ms as a function of the energy required to create capacitance in a liquid. In another embodiment, A1 may be about 0.5 milliamperes (mA) to 5 mA, the pulse width T1 may be about 200 microsecond (μs) and the period P1 may about 250 ms as a function of the energy to drive an LED or cause one or more pins 230, 351, 451 to vibrate.

In FIG. 5B a signal waveform 630 may be applied to a first LED 32A, 32B, 532 module or group and to the pins 230,351,451 and a second waveform 640 may be applied or used to energize a second LED 32A, 32B, 532 module and the pins 230,351,451, 352. The signal waveform 630 includes several square-wave pulses 632, 634, and 636 and the signal waveform 640 includes several square-wave pulses 642, 644, and 646. Each pulse 632, 634, 636, 642, 644, 646 may a have a similar magnitude and envelope. The waveform 630 may be used to energize a first LED 32A, 32B, 332 module and the pins 230,351,451 periodically P1 for a predetermined interval T1 where each pulse 632, 634, 636 has an amplitude A1. The waveform 640 may be used to energize a second LED 32A, 32B, 332 module and the pins 230, 351,451 periodically P2 for a predetermined interval T2 where each pulse 642,644,646 has an amplitude B1. The pulse width T1, T2 may be about 100 microsecond (μs) to 500 μsand the period P1, P2 may from 100 ms to 500 ms as a function of the energy to affect dermatological cells or chemicals 22A. In another embodiment, A1, A2 may be about 0.5 milliamperes (mA) to 5 mA, the pulse width T1, T2 may be about 200 microsecond (μs) and the period P1, P2 may about 250 ms as a function of the energy required to affect dermatological cells or chemicals 22A. In an embodiment the pulses 632, 634, 636 do not substantially overlap the pulses 642, 644, 646. In an embodiment T1>T2 and P2 is an integer multiple of P1.

FIG. 6 depicts a waveform 670 that includes multiple pulses 672, 674, 676, 678, 682, and 684 that may not overlap in the time or the frequency domain. In an embodiment each pulse 672, 674, 676, 678, 682, and 684 may have a pulse width T3, and frequency spectrum width F1 and period P3. The pulse 672 is frequency offset from the pulse 674, the pulse 676 is frequency offset from the pulse 678, and the pulse 682 is frequency offset from the pulse 684. The pulses 672, 674, 676, 678, 682, and 684 may be applied to an LED module to affect dermatological cells or chemicals 22A and the pins 230, 351, 451. Pulses 672, 674 having different frequency spectrums may enable different LED stimulation. In an embodiment the pulses 672, 676, 682 may be applied to a first LED module and the pulses 674, 678, 684 may be applied to a second LED module. The frequency separation between the respective pulses may enable simultaneous energization of a first and a second LED module and the pins 230, 351, 451 and subsequent and independent spectrum generation.

Figure 7A:
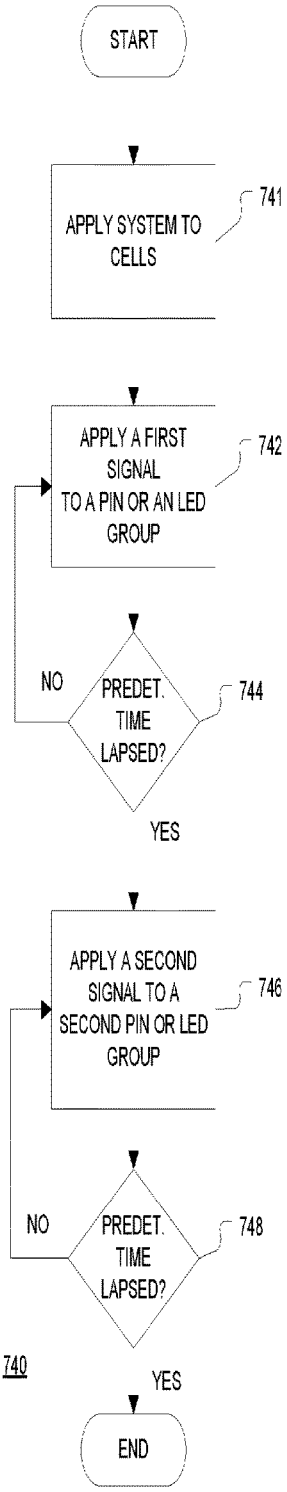
FIG. 7A-7C are flow diagrams illustrating dermatological treatment system processing algorithms according to various embodiments.

In an embodiment the invention may employ the algorithm 740 shown in FIG. 7A to apply therapy to dermatological cells. A user, clinician, or equipment may place an apparatus 10,320,360,360,400,460 on dermatological cells to be treated (activity 741) including pressing the apparatus against the cells firmly enough to embed one or more pins 251, 351, 451 in the cells. A first signal such as shown in FIGS. 5A, 5B, and 6 may be applied to a first LED module or group (32A) and the pins 230, 351, 451 of a dermatological apparatus 10, 320, 360, 360, 400, 460 (activity 742) for a predetermined time period (activity 744). A second signal such as shown in FIGS. 5A, 5B, and 6 may be applied to a second LED module or group (32B) and the pins 230, 351, 451 of a dermatological apparatus 10, 320, 360, 360, 400, 460 (activity 746) for a predetermined time period (activity 748). The signals applied to the groups may be selected to stimulate dermatological cells or chemicals 22A or cause vibration of one or more pins 251, 351, 451.

Figure 7B:
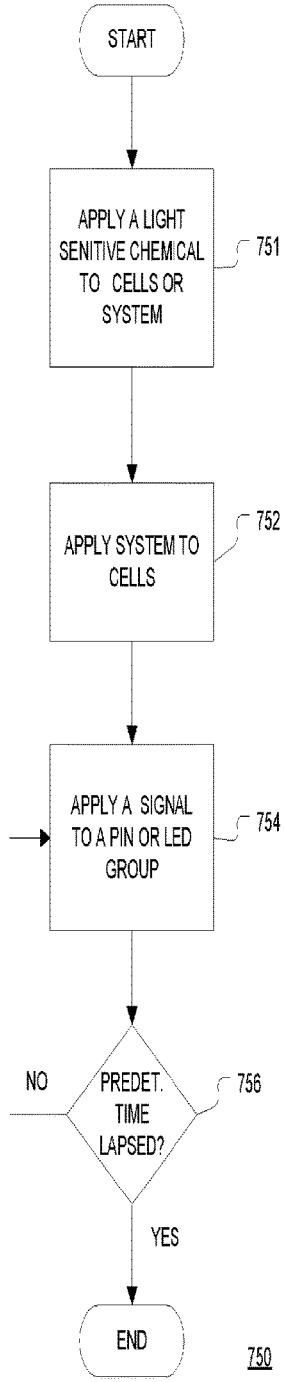

In another embodiment the invention may employ the algorithm 750 shown in FIG. 7B to apply therapy to dermatological cells. A user, clinician, or equipment may apply a light sensitive chemical on an apparatus 10, 320, 360, 360, 400, 460 or on dermatological cells to be treated (activity 751). The user, clinician, or equipment may place apparatus 10,320, 360, 360, 400, 460 on dermatological cells to be treated (activity 752). A signal such as shown in FIGS. 5A, 5B, and 6 may be applied to a LED module or group (32A or 32B) and the pins 230, 351, 451 (activity 354) for a predetermined time period (activity 356).

Figure 7C:
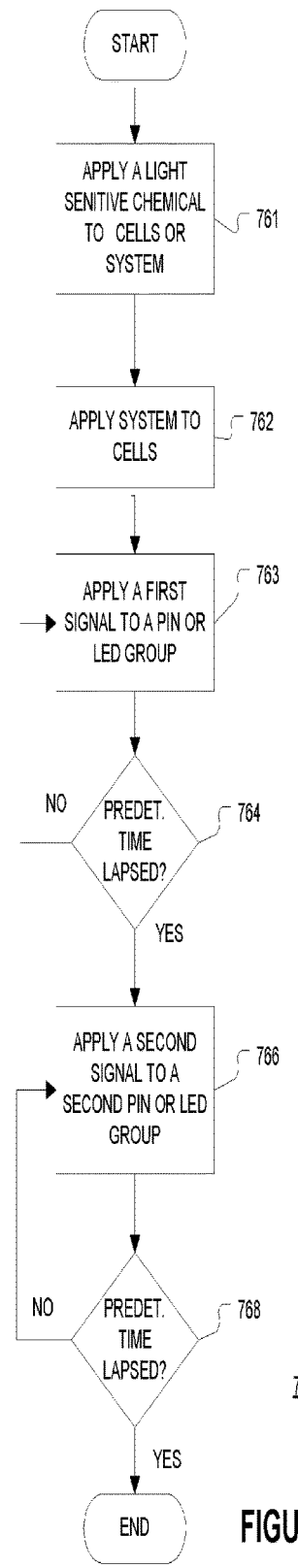

In another embodiment the invention may employ the algorithm 760 shown in FIG. 7C to apply therapy to dermatological cells. A user, clinician, or equipment may apply a light sensitive chemical on an apparatus 10, 320, 360, 360, 400, 460 or on dermatological cells to be treated (activity 761). The user, clinician, or equipment may place an apparatus 10, 320, 360, 360, 400, 460 on dermatological cells to be treated (activity 762). A first signal such as shown in FIGS. 5A, 5B, and 6 may be applied to a first LED module or group (32A) and one or more pins 251, 351, 451 of a dermatological apparatus 10, 320, 360, 360, 400, 460 (activity 763) for a predetermined time period (activity 764). A second signal such as shown in FIGS. 5A, 5B, and 6 may be applied to a second LED module or group (32B) and one or more pins 251, 351, 451 of a dermatological apparatus 10, 320, 360, 360, 400, 460 (activity 766) for a predetermined time period (activity 768).

The apparatus 10, 320, 360, 360, 400, 460 may be used to employ cosmetic or medications or other chemicals directly on dermatological cells such as skin with the addition of light of specific frequencies for treatment and healing of epidermal cells of the skin or tissue below the skin with the object of assisting the agents used in delivery, uptake, action and function more effectively. The LEDs 32A, 32B may create the specific frequencies of light. The apparatus 10, 320, 360, 360, 400, 460, light application may enable cosmetic or medication or other active chemicals 22A on dermatological cells for longer time periods while preventing dehydration of the applied substances. Such light application may improve the efficacy of cosmetic or medication or other active chemical as a function of the selected wavelengths or frequencies.

Further the dermatological system application may increase cellular activity and help heal tissue faster and facilitate the delivery, uptake and use in the cell of the cosmetics, medications, or chemicals 22A used. The LED light of specific frequencies may increase fibroblast production and collagen as well as other activities of the cell including stimulating the organells and mitochondria to produce ATP for cell energy for functioning, decreasing treatment time and facilitate healing. The apparatus 10, 320, 360, 360, 400, 460 make the agents used on the body more efficacious and useful to the body on a cellular level.

The apparatus 10, 320, 360, 360, 400, 460 may stimulate the basic energy processes in the mitochondria (energy compartments) of each cell, particularly when near-infrared light is used to activate the color sensitive chemicals (chromophores, cytochrome systems) inside but not limited to these spectrum alone as the UV, other visible and IR spectrums may also be usable. In an embodiment optimal LED wavelengths for skin repair may include 640, 680, 730 nanometers (nm) wavelengths to IR 880 nm Further application of blue light 400 nm to 490 via the apparatus 10, 320, 360, 360, 400, 460 may inhibit the growth and kill bacteria, fungus in and on dermatological cells. The apparatus 10, 320, 360, 360, 400, 460 may be employed to apply cosmetics, medications and/or other actives directly to the skin and maintain their presence long-term while using LED or other actinic light to increase their effect on the cells and tissue in the body. The apparatus 10, 320, 360, 360, 400, 460 are also highly portability and enable user mobility during treatment.

Chemicals 22A may include cosmetics, medications and other actives appropriate for dermatological cells including AHA's (alpha hydroxy acid), natural oils, aloe vera compounds, collagen boosters, bt, chitosan, daeses, endorphins, photodynamic drugs (PDT) like (Photofrin or ALA), vitamins A, C E or others, kojic acid, retinols or other exfoliant, salicylic acid, anti oxidants or other youth boosters and anti aging cosmetic or medications, antiseptic, antibiotics, anti-cancer agents, aroma therapy agents, fruit and vegetable extracts, anti-inflammatory agents, pain relievers, hormones, depilatories, and others, but the scope of this invention is not limited to these alone but can include any helpful medication, herbal formula or active compound for the skin and/or other tissues.

Figure 8:
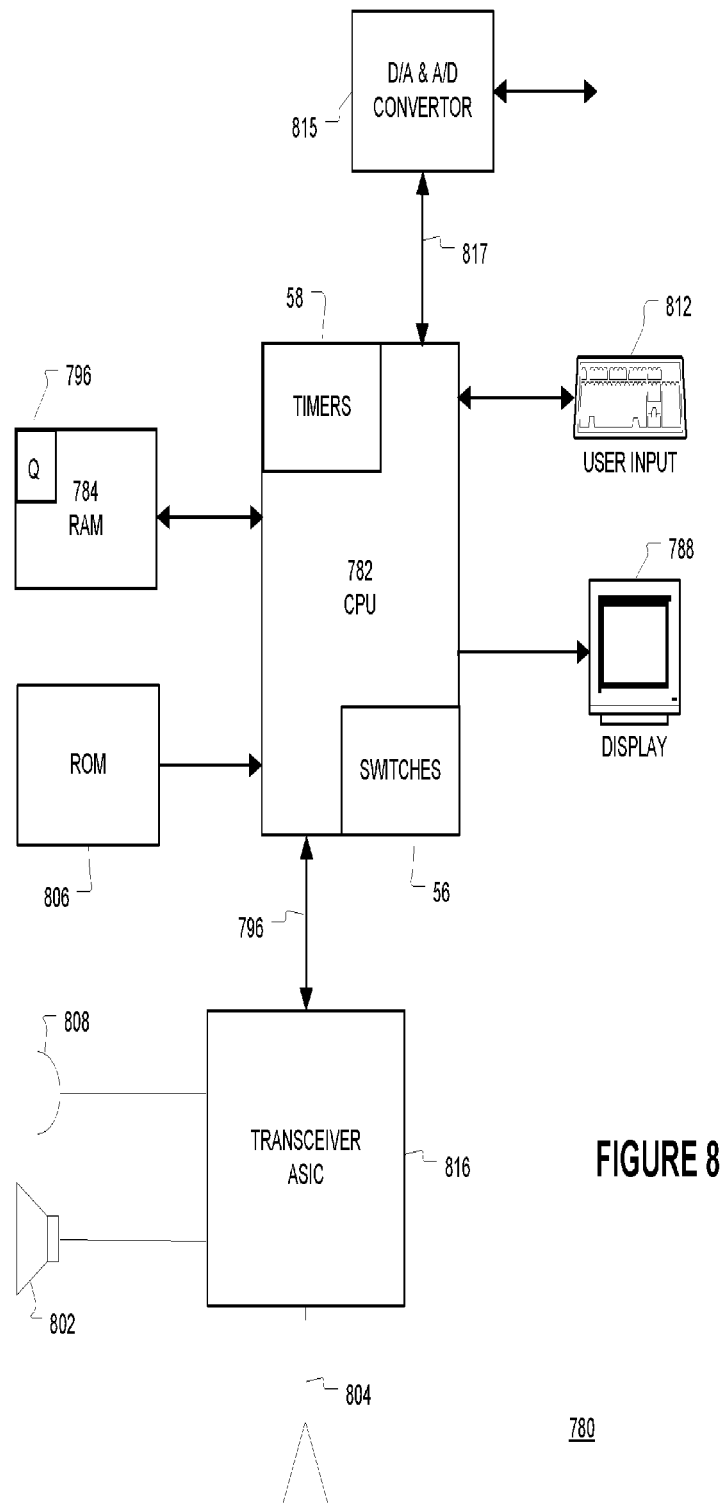
FIG. 8 is a block diagram of an article according to various embodiments.
Figure 9:
FIG. 9 is an image depicting potential side effects of conventional treatment prior art devices on skin.

FIG. 8 is a block diagram of an article 780 according to various embodiments. The article 780 shown in FIG. 8 may be used in various embodiments as a part of apparatus 10, 320, 360, 360, 400, 460 where the article 780 may be any computing device including a personal data assistant, cellular telephone, laptop computer, or desktop computer. The article 780 may include a central processing unit (CPU) 782, a random access memory (RAM) 784, a read only memory (ROM") 806, a display 788, a user input device 812, a transceiver application specific integrated circuit (ASIC) 816, a digital to analog (D/A) and analog to digital (AID) convertor 815, a microphone 808, a speaker 802, and an antenna 804. The CPU 782 may include an OS module 814 and an application module 813. The RAM 784 may include switches 56 and timers 58.

The ROM 806 is coupled to the CPU 782 and may store the program instructions to be executed by the CPU 782. The RAM 784 is coupled to the CPU 782 and may store temporary program data, overhead information, and the queues 798. The user input device 812 may comprise an input device such as a keypad, touch pad screen, track ball or other similar input device that allows the user to navigate through menus in order to operate the article 780.

The display 788 may be an output device such as a CRT, LCD, LED or other lighting apparatus that enables the user to read, view, or hear user detectable signals.

The microphone 808 and speaker 802 may be incorporated into the device 780. The microphone 808 and speaker 802 may also be separated from the device 780. Received data may be transmitted to the CPU 782 via a bus 796 where the data may include signals for an LED 32A, 32B, 332 or optical module or wires 331,458. The transceiver ASIC 816 may include an instruction set necessary to communicate data, screens, or signals. The ASIC 816 may be coupled to the antenna 804 to communicate wireless messages, pages, and signal information within the signal. When a message is received by the transceiver ASIC 816, its corresponding data may be transferred to the CPU 782 via the serial bus 796. The data can include wireless protocol, overhead information, and data to be processed by the device 780 in accordance with the methods described herein.

The DIA and AID convertor 815 may be coupled to one or more optical modules to generate a signal to be used to energize one of the optical modules. The DIA and AID convertor 815 may also be coupled to one devices such as LEDs 32A, 32B and the pins 251, 351, 451. Any of the components previously described can be implemented in a number of ways, including embodiments in software. Any of the components previously described can be implemented in a number of ways, including embodiments in software. Thus, the LEDs 32A, 32B, pins 251,351,451, controllers 54, switch 56, timers 58, controller 320 may all be characterized as "modules" herein. The modules may include hardware circuitry, single or multi-processor circuits, memory circuits, software program modules and objects, firmware, and combinations thereof, as desired by the architect of the system 10, 30, 50, 60 and as appropriate for particular implementations of various embodiments.

The apparatus and systems of various embodiments may be useful in applications other than a sales architecture configuration. They are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, single or multi-processor modules, single or multiple embedded processors, data switches, and application-specific modules, including multilayer, multi-chip modules. Such apparatus and systems may further be included as sub-components within a variety of electronic systems, such as televisions, cellular telephones, personal computers (e.g., laptop computers, desktop computers, handheld computers, tablet computers, etc.), workstations, radios, video players, audio players (e.g., mp3 players), vehicles, medical devices (e.g., heart monitor, blood pressure monitor, etc.) and others. Some embodiments may include a number of methods.

It may be possible to execute the activities described herein in an order other than the order described. Various activities described with respect to the methods identified herein can be executed in repetitive, serial, or parallel fashion.

A software program may be launched from a computer-readable medium in a computer-based system to execute functions defined in the software program Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly or C. The software components may communicate using a number of mechanisms well known to those skilled in the art, such as application program interfaces or inter-process communication techniques, including remote procedure calls. The teachings of various embodiments are not limited to any particular programming language or environment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim Rather, inventive subject matter may be found in less than all features of a single disclosed embodiment. Thus the following claims are hereby incorporated into the Detailed Description, with each claim standing on its own as a separate embodiment.

An objective of the present invention is to provide a therapeutic method and system that may be employed to reduce hypervascularity in dermis or epidermis by generating desirable thermal damage thereto or inducing phagocytosis or apoptosis of vascular cells in order to treat melasma, dermal melasma, hyperpigmentation, hypopigmentation, rosacea, flushing, erythema, or telangiectasia while lowering the risk of excessive heating of skin encountered in and reducing the rate of re-occurrence associated with conventional treatments including LASER treatments for melasma, dermal melasma, hyperpigmentation, hypopigmentation, rosacea, flushing, erythema, or telangiectasia.

In accordance with a stated objective, the present invention may provide an system or system for treating vessels, such as blood vessels in skin. The system may including two or more electrodes sized to be inserted into skin to deliver electrical signals to a vessel therein to be treated. The system may include an electrical signal generator electrically coupled to the electrodes and a power supply unit for supplying power to the electrical signal generator. In an embodiment, electrical signals delivered to the electrodes may be a repetitive or periodic electrical signal with at least one delay or off duty time.

In an embodiment, a target skin vessel may be positioned between two electrodes. Additionally, electric fields may be formed between the two or more electrodes. The electric field may formed from an alternating current (A.C.) signal applied the electrodes. In addition, some of the electrodes may form bipolar configurations. Additionally, the two or more electrodes may be inserted adjacent to a targeted skin vessel. The application of the system to skin blood vessels may be used to treat one or more symptoms of various skin conditions including melasma, dermal melasma, hyperpigmentation, hypopigmentation, rosacea, flushing, erythema, and telangiectasia. Further, the system may be used to one or more symptoms of various other health conditions by affecting vessels associated with hair loss, hair removal, excessive sebaceous gland secretion, excessive sweating (hyperhydrosis), and axillary osmidrosis.

In an embodiment, an electrical signal delivered through the two or more electrodes into skin may induce a thermal effect on a target skin vessel in a region of skin penetrated by the electrodes. Further, an electrical signal delivered through the electrodes into the skin may induce a thermal effect on an outer layer of a target vessel in region of the skin penetrated by the electrodes. Additionally, a thermal effect may be induced independently around each electrode to the vessel located in region of the skin penetrated by each electrode. Further, a thermal effect may not be generated by an electrical signal conducted in an area between electrodes including an area around a vessel in the area of the skin penetrated by the electrodes. In an embodiment, electrodes may be inserted into dermal layer of the skin.

In addition, an embodiment of the electrical signal generator may include a high-frequency signal generator and generate signals having a frequency is from 0.1 MHz to 100 MHz. Further, an embodiment of the electrical signal generator may include a radio frequency signal generator. In addition, in an embodiment various operational parameters including the depth of electrode penetration into the target skin, the voltage level to be applied to electrode, the power to be transmitted to electrode, the duration over which an electrical signal is to be emitted to electrode, and the delay time during which electrical signal is not to be emitted to an electrode, may be set preliminarily.

Further in an embodiment, the system may include an electrode module that includes an array, which the electrodes may be fixed. In addition, the system may include a motor unit for driving or moving the array including two or more electrodes to penetrate a desired region of skin. It is noted that the system may be used for vessel treatment in various tissue in all anatomical regions in addition to dermatologic regions.

In an embodiment, a system of the present invention may not only allows its users to treat hypervascularity in the dermis or epidermis to be normalized by generating thermal damage thereto or inducing phagocytosis or apoptosis of vascular cell in order to treat melasma, dermal melasma, hyperpigmentation, hypopigmentation, rosacea, flushing, erythema, or telangiectasia, but also to accurately control the degree or level of thermal injury delivered to a vessel directly via an electrode inserted in the skin. Applying heat selectively to a vessel in the skin, instead of applying heat to the entire skin, may reduce the adverse effects caused by overheating of the skin, such as burns, which are common in conventional treatments for melasma, dermal melasma, hyperpigmentation, hypopigmentation, rosacea, flushing, erythema, or telangiectasia. Eliminating or removing a vessel in the skin may also lower the rate of re-occurrence associated with conventional treatments for melasma, dermal melasma, hyperpigmentation, hypopigmentation, rosacea, flushing, erythema, or telangiectasia. Hereinafter, the present invention will be described with reference to the drawings. Like elements in the drawings are represented by the same reference numerals when possible. In the following description, well-known functions or unnecessary explanation about configurations are not described in detail since they would obscure the subject matter of the present invention.

According to recent studies conducted by the present inventor, lesions of melasma, dermal melasma, hyperpigmentation, hypopigmentation, rosacea, flushing, erythema, or telangiectasia, as well as hair loss, hair removal, excessive sebaceous gland secretion, excessive sweating, and axillary osmidrosis, are related to the number, size, shape, and function of vessels therein. For example, melasma, pigmentation, rosacea, flushing, and telangiectasia lesions clinically and histologically show significant increases in the number and size of blood vessels in the dermis or epidermis, compared to nearby normal skin.

The inventor notes that altering blood vessels in these lesions according to treatment purpose has been found to help to treat those states thereof. In addition, the inventor notes that hair loss may be treated by increasing blood circulation to hair follicles lacking blood supply, while excessive sebaceous gland secretion and excessive sweating may be treated by diminishing abnormal increases in the number and size of vascular structures to target glands.

The inventor also notes that while rosacea, flushing, erythema, and telangiectasia are generally known to be symptoms of underlying vascular problems, melasma, dermal melasma, hyperpigmentation, and hypopigmentation lesions are closely related thereto.

Moreover, the inventor has noted excessive development or deterioration of blood vessels that supply nutrition to structures in skin important to hair loss, hair removal, excessive sebaceous gland secretion, excessive sweating, and axillary osmidrosis.

Accordingly, the present invention has been developed to transmit electrical signals to vessels in skin through invasive electrodes for selective treatment of vessels including blood vessels. The inventor notes that blood vessels have a particularly higher impedance relative to the surrounding skin tissue enabling selective treatment of some tissue in skin due to the differences of tissue impedance, conductivity, and dielectric permittivity between individual layers of skin tissue, vessels, and appendages.

The present invention can control the intensity of electric signals that are emitted in electrodes in order to control degree of thermal reaction induced on nearby tissue including vessels. This may allow user to selectively achieve various desired effects including congestion, regeneration, remodeling, growth, regrowth, degradation, or degeneration of vascular structures in skin. Accordingly, a system of the present invention may be employed to treat melasma, dermal melasma, hyperpigmentation, hypopigmentation, rosacea, flushing, erythema, telangiectasia, hair loss, or enable hair removal via skin vessel treatment. Additionally, embodiments of the present invention may be used to treat excessive sebaceous gland secretion (hyperseborrhea), excessive sweating (hyperhidrosis), or related disorders, such as axillary osmidrosis.

Further, embodiments of the present invention may enable a user to effectively treat hyper- or hypovascularity in dermis, epidermis, or skin appendage by generating optimal thermal effects on target vessel therein, or by inducing phagocytosis or apoptosis of target vascular cells. Embodiments of the present invention may also be employed to prevent or reduce common side effects of too much heat being applied to vessel, or reduce recurrence rate of lesion caused by rebounded hyperplasia of removed vessel after conventional treatments.

Embodiments of the present invention may provide a system for treating melanocyte or basement membrane in skin by improving pathological structure or function, or a system for affecting on amount or function of vascular endothelial growth factor (VEGF), which is derived from vessels. As noted conventional invasive high-frequency devices may be limited to coagulating skin with heat for primary purpose of neocollagenesis, hemostasis, and cauterizing vessel directly with high heat. Unlike conventional devices, the present invention encompasses an system for treating vessel in skin by forming electric field within skin. In an embodiment, the system forms an electric field via two or more electrodes that penetrate skin.

In an embodiment an electric field may be uniformly formed in skin via an electrical signal emitted therein to induce thermal effect on blood vessel first rather than surrounding skin tissue. Thus, unlike the direct electrocauterization of blood vessels, an electric signal that forms a uniform electric field may facilitate selective heating of blood vessels, enabling the treatment of various lesions caused by abnormal vascularity. While conventional invasive high-frequency devices which are aimed at stimulating collagen production in skin require the application of a relatively long conduction time, embodiments of the system of the present invention may utilize or generate much shorter conduction time. Moreover, in addition to conduction time, embodiments of the system of the present invention may control other treatment parameters, including signal voltage, power, impedance in skin, etc. as appropriate.

As noted due to their high conductivity, blood vessels may be coagulated first before epidermis or dermis is coagulated via embodiments of the present invention. In an embodiment, the shortest signal conduction times employed by system to selectively coagulate blood vessel may be 50 msec, more generally within 100 msec, or even up to within 300 msec.

In order to prevent excessive thermal damage to non-targeted tissue or to concentrate the desired thermal effect on a target vessel, an electrical signal may have one or more pulses (repeated) with a conduction time and delay time (for example, 5-100 msec) before the next pulse. By employing a repetitive electrical signal with delay time, the applied voltage may be increased, allowing for a greater distance between electrodes (153). Also, the greater voltage (of an applied signal) can increase the degree of thermal effect on blood vessels via a shorter conduction time, thereby minimizing unwanted injury to surrounding tissue due to their lower resistance as noted.

In an embodiment, delay time (between active pulses) may allow for a greater applied voltage, which may induce a faster reaction from blood vessel, thereby preventing/limiting undesired thermal injury to surrounding tissue that may likely occur from sustained delivery of electrical energy. In an embodiment, a conduction time of a repetitive electrical signal may be varied according to configuration of parameters of the system, where the signal conduction time may be set to be the same or different in each cycle. Also, the length of delay time (off duty cycle) may also be varied in the same manner.

Additionally in an embodiment, the conduction time may be varied as a function of the electrical signal's set voltage, electric power, and electric current, as well as the size, thickness, and quantity of target vessels in skin. Further, the electrode insertion depth and thickness, distance between electrodes, and deployment of electrodes relative to the target vessel may also vary the conduction time. In an embodiment, the electrode may be arranged to deliver electrical signals in a bipolar configuration that may be employed in all cases of vessel treatment, except for direct electrocautery of blood vessel.

As noted, melasma, dermal melasma, pigmentation, rosacea, flushing, or telangiectasia lesions clinically and histologically show significant increases in the number and size of blood vessels in dermis or epidermis, compared to normal peripheral skin. The vascular changes apparent in melasma, dermal melasma, pigmentation, rosacea, flushing, or telangiectasia may be due to angiogenesis or vasodilation in association with VEGF (Vascular Endothelial Growth Factor) production. In melasma, dermal melasma, pigmentation, rosacea, flushing, or telangiectasia, abnormal vascularity in the lesion may act as a main reason of incidence or aggravation, because the number of blood vessel distributed throughout the lesions has been shown to be significantly related to the amount of pigment therein. In an embodiment, a system may be employed to reduce target vessel including neovascularization, vessel dilation, or hypervascularity that causes the above conditions.

The system for generating electrical signals according to the exemplary embodiments described below with respect to FIG. 9 through FIG. 21 may be substantially similar in various respects to the dermatological treatment apparatus as described above with respect to FIG. 1A through FIG. 8 of the present application, and the disclosure thereof is incorporated herein by reference. Likewise, the disclosure with respect to the system for generating electrical signals described in connection with FIG. 9 through FIG. 21 is incorporated by reference into the exemplary embodiments described with respect to FIG. 1A through FIG. 8 above.

Figure 10:
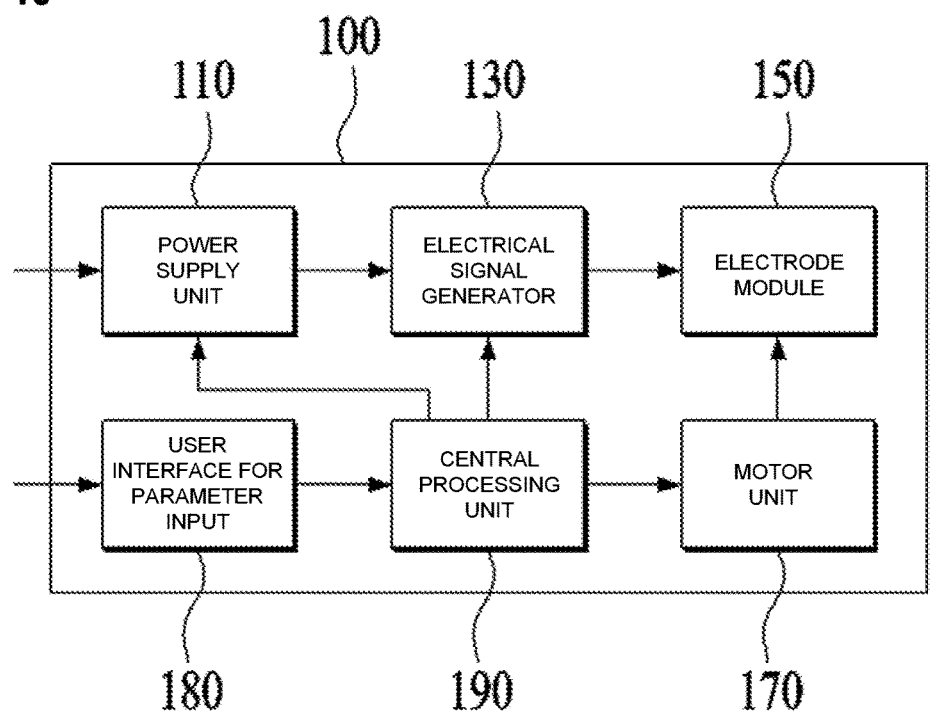
FIG. 10 is a simplified block diagram of a system for generating electrical signals to treat vessel in skin according to various embodiments of the present invention.

FIG. 10 is a simplified block diagram of a system 100 for generating electrical signals to treat vessels in skin according to various embodiments of the present invention. As shown in FIG. 10, the treatment system (100) for generating electrical signal with which to treat vessels in skin, according to an embodiment of the present invention, may include a power supply unit (110), an electrical signal generator (130), an electrode module (150), a motor unit (170), a user interface for parameter input (180), and a central processing unit (190).

Figure 11:
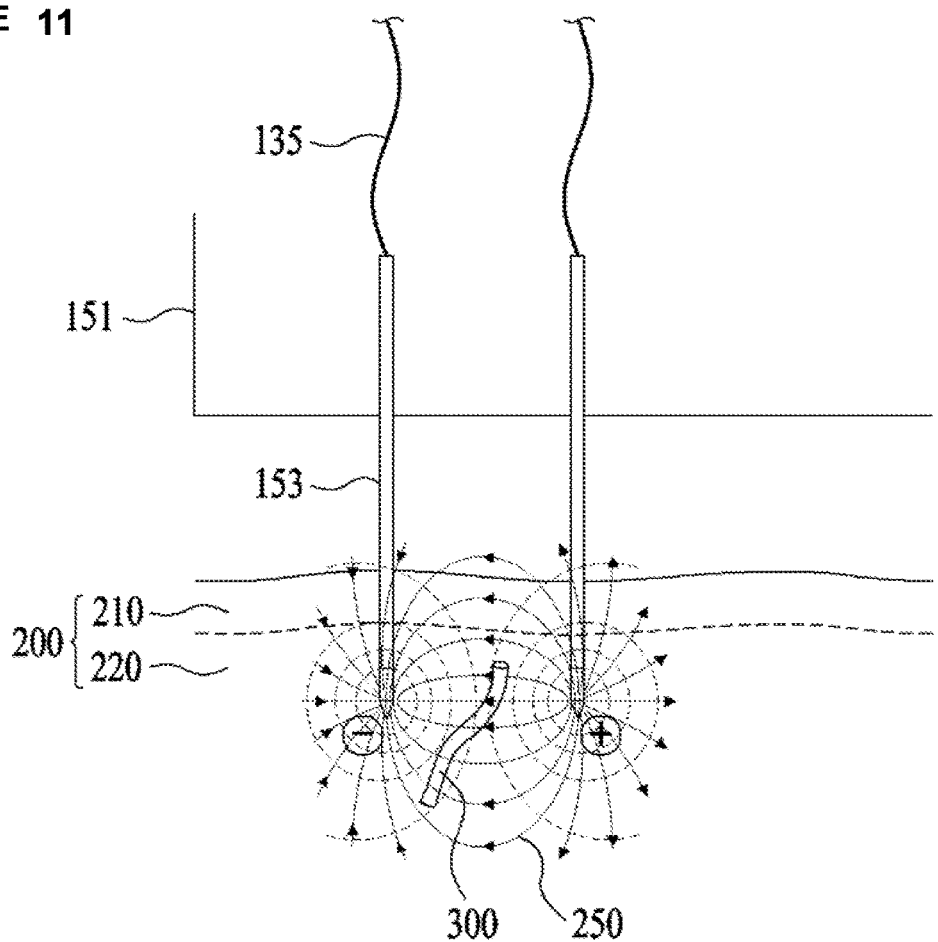
FIG. 11 is a simplified illustration of vessel treatment via system delivering electrical signals according to various embodiments of the present invention.

The electrode module (150) may include a fixed portion (FIG. 11, 151) to which two or more electrodes (FIG. 11, 153) are attached. The power supply unit (110) may supply power from outside the system 100 to the electrical signal generator (130) and other components. The electrical signal generator (130) may deliver/generate electrical signals that are conducted by one or more electrode (153) of the electrode module (150) via an electrically conductive material, such as an electrical signal transmission line (FIG. 11, 135). In an embodiment, an electrode (153) may also be connectable directly or indirectly with the electrical signal generator (130) or the motor unit (170), omitting an electrode module (150). In addition in an embodiment, either the electrode (153) or the electrode module (150) may be directly or indirectly connectable electrically to the electrical signal generator (130). In an embodiment, the electrode (153) may be needle shaped and composed of a conductive material.

In an embodiment, the electrical signal generated by the electrical signal generator (130) may be an electromagnetic wave with a frequency ranging from 300 Hz to 300 GHz. In an embodiment, the electrical signal generator (130) may generate an intermediate frequency, a high frequency, and a radio frequency electromagnetic wave or ultrasonic wave. The electrical signal generated by the electrical signal generator (130) may be emitted in the form of an electromagnetic wave of a predetermined frequency. The electrical signal may be transferred to two or more electrodes (153). Heat may then be generated on or around target vessel (300) by transmission of the electrical signal into the lesioned area of the skin (200) via the electrode (153).

In an embodiment, an operator may insert electrodes (153) directly into the lesioned skin (200) by hand, or electrodes (153) may be attached to the electrode module (150) for insertion. In an embodiment, the system 100 may include a motor unit (170) that may automatically drives/insert the electrode (153) or the electrode module (150) to which the electrode (153) is coupled to a predetermined depth into skin (200, FIG. 11). The motor unit (170) may be connected directly or indirectly to the electrode (153) or electrode module (150).

In an embodiment, the electrodes (153) or electrode module (150) may not be connected to the motor unit (170) before insertion into skin (200). It may be inserted into skin (200) by pressing or attaching the electrodes (153) or the electrode module (150) to the motor unit (170) prior the electrode penetration phase. A motor unit (170) may transmit directly or indirectly the force that drives two or more electrodes (153) to penetrate into the skin (200) to a predetermined depth (approximately 1 mm to 2.5 mm in an embodiment). In an embodiment, two or more electrodes (153) may be inserted into the skin (200) so they penetrate the epidermal layer (210) at a predetermined depth of approximately 0.2 mm to 1 mm or the dermal layer (220) at a predetermined depth of approximately 1 mm to 4 mm. The insertion depth of the electrode (153) into target skin (200) may range from 0.2 mm to 4 mm as a function of the patient in an embodiment.

It is noted in an embodiment that it may also be possible to treat a target vessel by placing electrodes (153) on the surface of the skin (200) versus penetrating into skin (200). As described above, the depth of electrode (153) insertion into target skin (200) may be within 4 mm. However, the depth of insertion of electrodes (153) into skin (200) may be deeper than 4 mm in targeted area where skin thickness is relatively thicker and could correspond to the entire thickness of the skin (200) layer. In an embodiment, electrodes (153) or the electrode module (150) may be moved linearly via the motor unit (170), where the motor unit 170 may include an actuator, a motor, a linear motor, a stepping motor, an electromagnet, or a piezoelectric element. In an embodiment, a user via the user interface (180) may able set several parameters related to the system I 00 including the magnitude of the signal voltage, current, the resistance value, the impedance of the target tissue, and the electrical conduction time, and the depth of electrode 153 insertion into skin 200. Upon receiving a control command from the user interface (180), the central processing unit (190) may direct the electrical signal generator (130) to deliver/generate signals having the desired parameters to two or more electrodes (153), in an embodiment, or based on the parameters including electrical current, the resistance value, the impedance, or the electrical conduction time to control the energy amount of the electrical signal.

Figure 21:
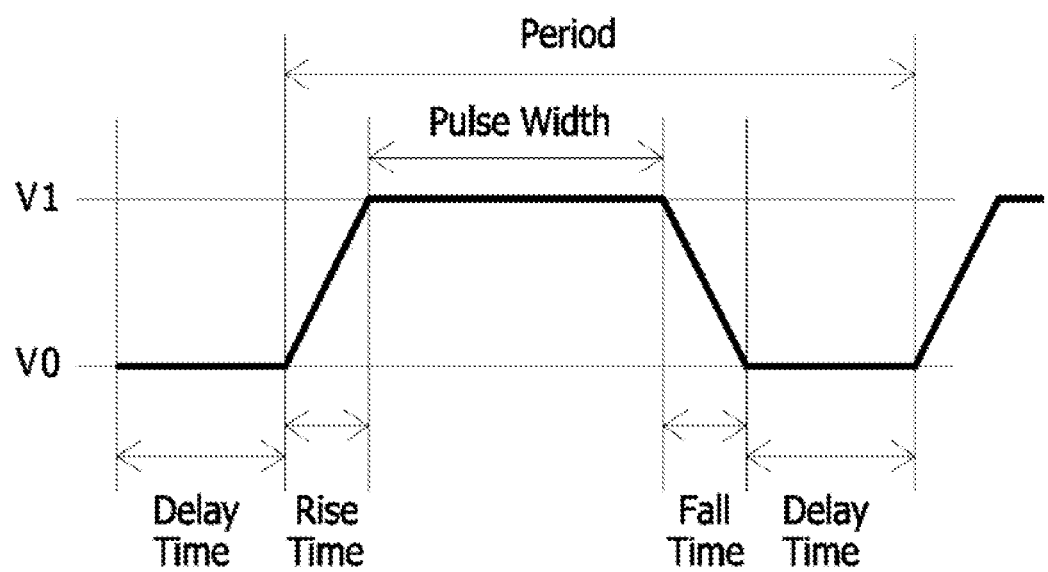
FIG. 21 is a simplified diagram of a waveform of an electrical signal that may be generated by a system for generating electrical signals to treat vessel in skin according to various embodiments of the present invention.

Additionally, the central processing unit (190) may control the power supply unit (110) so that it repeatedly supplies power to the electrical signal generator (130) over a predetermined time interval. FIG. 21 is a simplified diagram of a waveform of an electrical signal that may be generated by the system I 00 for generating electrical signals to treat vessels in skin 200 according to various embodiments of the present invention. In an embodiment, the central processing unit (190) may control the electrical signal generator (130) such that it generates an electrical signal repeatedly at predetermined time interval as shown in FIG. 21.

In an embodiment, the applied voltage (VI, FIG. 21) may be in the range of 10 volts to 400 volts (preferably 20 to 300 volts), based on a 100-ohm load. A delay time (or off duty cycle) may be in the range of 0.1 msec (millisecond) to 500 msec (preferably 5 to 300 msec). A conduction time (on duty cycle) may be in the range of 1 msec to 450 msec (preferably 5 to 300 msec). In an embodiment, if the delay time is too short (less than 0.1 msec), undesired thermal damage may occur in non-target tissues (other than target vessel (300)), whereas too long of a delay time (longer than 500 msec) would be too long to induce a enough thermal response on target vessel (300). Conversely, if the conduction time is too long (greater than 450 msec), excessive heat may be generated on tissues other than the target vessel (300, FIG. 11).

Similarly, if the conduction time is too short (less than 1 msec), the thermal response elicited or generated in target vessel (300) may be insufficient to provide the desired effect or treatment.

In an embodiment, the total treatment time (equal to the number of repeated cycles of the electrical signal conduction and the delay times) may be closely related to the selected system parameters including the applied voltage, electric power, conduction time, and delay time. If treatment time is too short (too few a number of the cycles), the system 100 may fail to generate a sufficient, desired thermal response, whereas too long a treatment time (too many cycles) may cause excessive, undesired thermal damage to other tissues and the target vessel (300). In an embodiment, a desired therapeutic effect may achieved via the application of a pulsed signal as shown in FIG. 21, in particular with a pulsed signal having relatively high output voltage versus a lower output voltage signal that is continuously applied.

Accordingly, the system 100 may engage the electrical signal generator (130) to generate a pulse type of electrical signal. In an embodiment, the pulsed signal may be alternating current (A.C.) versus a direct current (D.C.) pulse to generate a desired thermal response. In an embodiment, when two electrodes 153 are inserted into the skin around a target vessel (300) as shown in FIG. 11, the signal applied to the electrodes (153) may form a bipolar configuration (one electrode acting as an anode, the other as the cathode. Further in an embodiment, an Alternating Current Pulsed-typed Electric Field may be formed in the skin, by applying an A.C. pulsed electrical signal via the electrode (153) inserted into skin where the electrodes form a bipolar pair and the use of an A.C. signal causes the electrode polarity to switch periodically, i.e, the anode becomes the cathode, and the cathode becomes the anode in a repeated pattern.

In an embodiment, the signal applied to the electrode pair 153 may be a high-frequency pulsed A.C. polarity signal, which may be much more effective at vibrating water molecules in skin than a high frequency pulsed D.C. polarity signal and, thereby, generating a greater desired thermal response in target vessels (300). In an embodiment, the use of an alternating polarity, high-frequency pulsed signal (of A.C. polarity) may allow for generating selective thermal response to target vessel (300), compared to the use of a non-alternating polarity high-frequency pulsed signal (of D.C. polarity).

Accordingly, in the present invention, the electric field (250) formed between two electrodes (153) inserted around target vessel (300) as shown in FIG. 11 may be preferably alternate or be an alternating current (A.C.) electric field due to the application a high-frequency pulsed A.C. polarity signal to the electrode 153 via the electrical signal generator 130. In an embodiment, when a high output voltage is applied to the electrodes 153 operating a bipolar configuration, a uniform and strong electric field may be formed in a wider area, compared to when a low output voltage is applied to the same electrodes 153. In an embodiment, the thermal response elicited on target vessel (300) may occur more rapidly in the presence of an electric field generated from a high output voltage signal. In such an embodiment the signal pulse width (conduction time) may be made smaller when a high output voltage signal is employed.

As noted in an embodiment, a user may be able to set/select the insertion depth of electrodes (153) into skin (200) via the user interface (180). In an embodiment, the central processing unit (190) may control the degree to which the motor (170) moves the electrode (153) to ensure the electrodes 153 are inserted to the desired depth. As also noted in an embodiment, a user via the user interface (180) may input system parameters including the signal voltage, power, and conduction time and set the insertion depth for electrodes (153). In an embodiment, the central processing unit (190) may control the electrical signal generator (130) so it generates the predetermined or desired electrical signal. In an embodiment, an A.C. or D.C. signal received from the power supply unit (110) may be converted into a predetermined/desired electric signal by the electrical signal generator (130). The resultant electrical signal may be transmitted/applied to electrodes (153).

As noted in an embodiment, the central processing unit (190) may control the motor unit (170) to drive or move individual electrodes (153) or the electrode module (150) into the skin (200) to a desired location or depth according to the electrode (153) insertion depth set by the user through the user interface (180). FIG. 11 is a simplified illustration of a mechanism of vessel (300) treatment via a system (100) delivering electrical signals according to various embodiments of the present invention. As drawn in FIG. 11, skin (200) may include an epidermal layer (210) and a dermal layer (220). In an embodiment, the dermal layer (220) is primarily where target vessel (300) resides that gives rise to melasma, dermal melasma, pigmentation lesion, rosacea, flushing, and telangiectasia.

In another embodiment, a target vessel (300) may be distributed in the epidermal layer (210), while in a further embodiment, a target vessel (300) may be distributed throughout both the epidermal layer (210) and the dermal layer (220). Accordingly, electrodes (153) may be inserted within the epidermal layer (210) only or further into the dermal layer (220) as needed, depending on the distribution of target vessel (300) throughout the skin.

In an embodiment, vessels (300) that give rise to melasma, dermal melasma, hyperpigmentation, hypopigmentation, rosacea, flushing, erythema, or telangiectasia lesions are referred to target vessel (300). As shown in FIG. 11, when target vessel (300) are present only in the dermal layer (220), it may be preferable that the inserted electrodes (153) penetrate the dermal layer (220). In an embodiment, however electrodes (153) may be inserted such that they penetrate only the epidermal layer (210) with appropriate energy setting (voltage, power, and conduction time) and still effectively treat the target vessel. As noted in an embodiment, it may be possible to generate a sufficient thermal response in a target vessel (300) via electrodes (153) placed on the surface of the skin.

For treating melasma, dermal melasma, pigmentation, rosacea, flushing, or telangiectasia lesions in the dermal layer (220), electrodes (153) may be inserted into the dermal layer (220) among target vessels (300) within the lesioned area of the skin in an embodiment. In an embodiment, two electrodes (153) may be inserted into the skin about a target vessel (300) (positioned between two electrodes (153)). In such an embodiment, an electric field (250), as shown in FIG. 11, may be formed between the two electrodes (153) as a function of the applied signal. In an embodiment, a target vessel (300) may still receive desired thermal exposure or have a desired thermal response when located deeper than the electrode (153) can penetrate or positioned immediately beneath the electrode (153), as long as the target vessels (300) are located within the electric field (250) formed between the electrodes (153).

In an embodiment, the electrodes (153) may be inserted into the skin with target vessel (300) positioned in an A.C. electric field (250) formed between two electrodes (153) based on application of an A.C., high frequency, pulsed signal. Such an embodiment may conduct a high-frequency signal of A.C. polarity between two electrodes (153) operating in a bipolar configuration to induce a selective/desired thermal response in target vessel (300) positioned between the two, bipolar electrodes (153). In an embodiment, such a treatment may limit treatment to the vessel 300 while sparing injury to surrounding tissue. In an embodiment, it may be preferable that the high-frequency signal applied to the electrode (153) has a main operating frequency between 0.1 MHz and 100 MHz.

It is noted that in some instances a target vessel (300) may be positionable relatively close or adjacent to one or more electrodes (153) while other times a target vessel (300) may be relatively far from one or more electrode (153). In such embodiments, a user may change the type of electrical signal or adjust the voltage, power, or conduction time of the electrical signal applied to the electrodes 153 based on their distance from a target vessel (300). As noted and show in FIG. 11 in an embodiment electrode (153) may be inserted into skin (200) and receive electrical signals via the electrical signal transmission line (135) causing the electrical signal transmitted to the inserted portion of the electrode (153) to be emitted to the blood vessel (300). In an embodiment, the electrical signal transmission line (135) may be connected directly to the electrode (153) or indirectly via a printed circuit board, a solder, an electrical pin (a pin that is capable of conducting electric power and being bent and stretched), a pogo pin, an electric conduction plate, an electric conduction rod, or an electrical connector to transmit electrical signal (not shown).

In an embodiment, electrical signals applied to a lesion may be concentrated to target vessel (300) in the skin, generating heat in the target region, which heat treat target vessel (300) and thus form a therapeutic mechanism. As noted in an embodiment system (100) may be employed to deliver electrical signals to electrode (153) inserted into the skin or in contact with the skin surface in order to generate thermal injury on or around target vessel (300) in the skin. Through clinical experiments with the treatment system (100) for generating electrical signal with which to treat vessel in the skin, the inventor notes that the causative target vessel (300) that give rise to lesions, such as melasma, dermal melasma, pigmentation, rosacea, flushing, or telangiectasia, are mostly neovascular (premature blood vessel), and the binding between the cells that constitute their vessel walls is in a loose state, relative to normal vessels. Moreover, the thickness of the vessel wall for neovasculature is thinner than that for normal blood vessels, and the cellular structures in the vessel wall are weak. Thus, unlike normal blood vessels, these immature blood vessels can be easily destroyed by relatively weak electrical stimulation.

Accordingly, by applying electrical signals via the system 100 to destroy the causative, target vessel (300) that give rise to lesions, such as melasma, dermal melasma, pigmentation, rosacea, flushing, or telangiectasia, treatment for these conditions may be possible although not simple. To induce suitable damage on target vessel (300), an electrical signal that is neither too weak nor too strong are required to be applied via the system 100. Therefore, in an embodiment delicate control of the electrical signal generator (130) is required. Since target vessel (300) of neovascularity may be treated with relatively weak signals employment of strong electrical signals may result in artificial stimulation, cauterization, elimination, or severe destruction, and compensation mechanisms that may quickly give rise to more new vessels due to a phenomenon known as vascular hyperplasia.

Consequently, treatment methods aimed at simply destroying the causative, target vessel (300) in melasma, dermal melasma, pigmentation, rosacea, flushing, or telangiectasia lesions via electrical signal of random strength may result in treatment outcomes of vascular hyperplasia or post-inflammatory hyperpigmentation (PIH), a condition that further exacerbates lesions of melasma, dermal melasma, pigmentation, rosacea, flushing, or telangiectasia.

Figure 12:
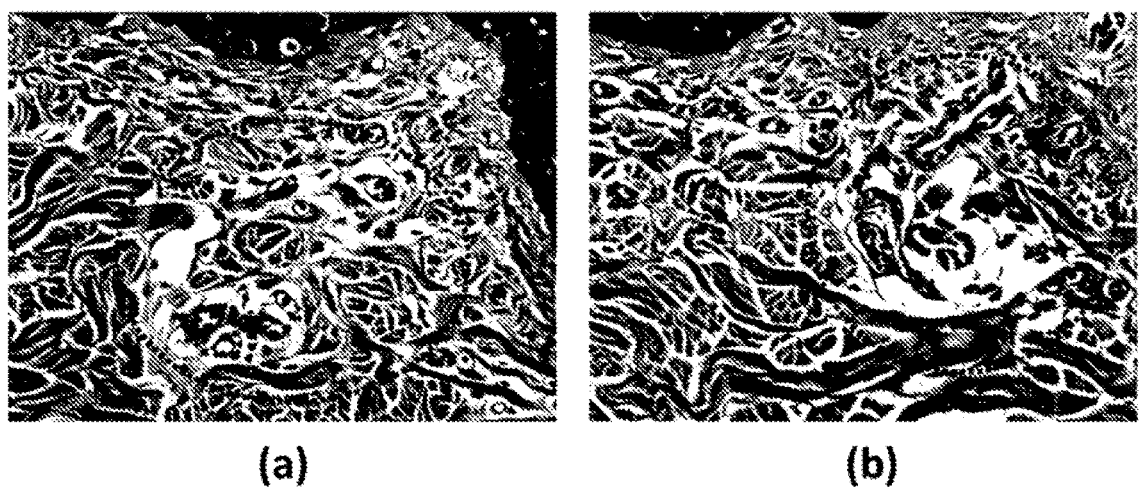
FIGS. 12 to 20 are images depicting the clinical effects of employing a system for delivering electrical signals to vessels in skin during animal experiments according to various embodiments of the present invention.
Figure 13:
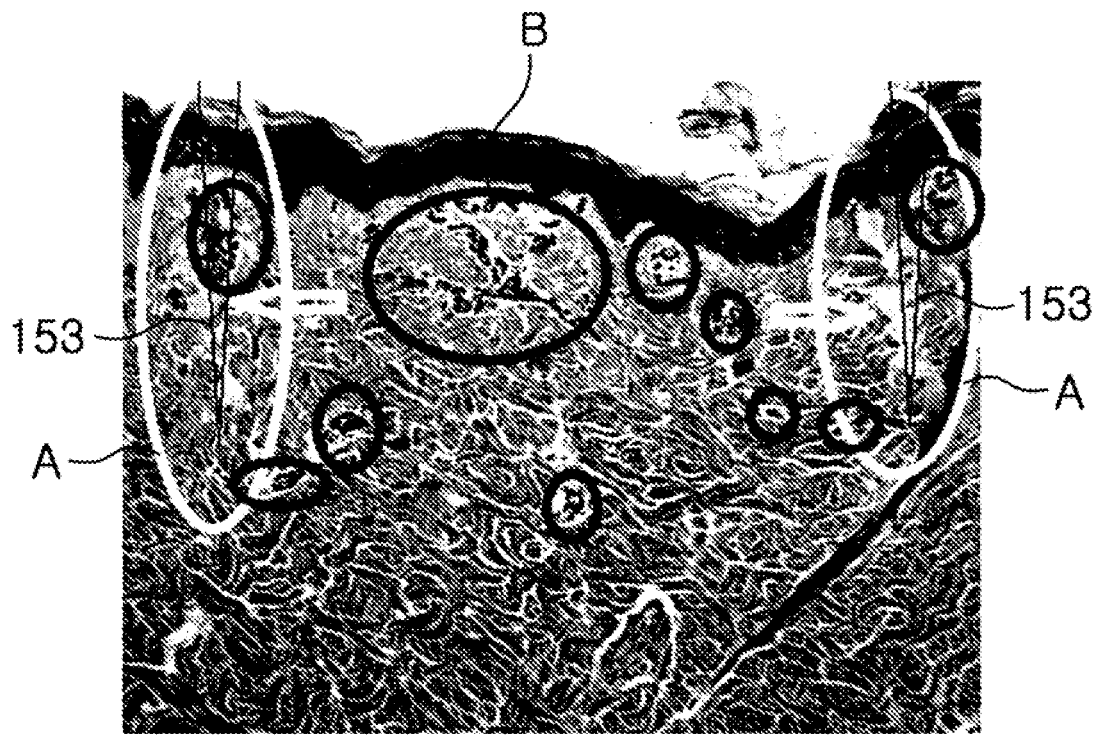
Figure 13:
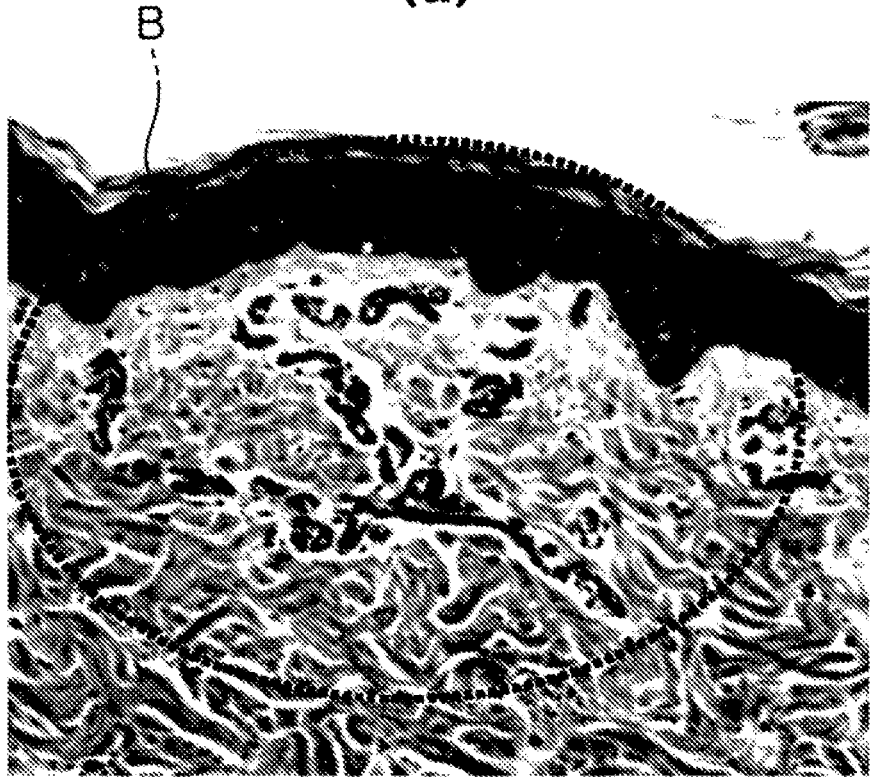

As shown in FIGS. 12 and 13, when the therapeutic system (100) of the present invention is used to apply electric signals to the skin of a micro pig, vessels in dermal layer of skin responded selectively with the signal. No evidence that the blood vessels were destroyed or that excessive bleeding occurred was recorded. In particular, in FIG. 13(a), heat-damaged tissue (pale pink in color) is observed in regions demarcated by white ovals labelled region A, around which electrodes (153) have been inserted. The black circles labelled as region B highlight areas of selective thermal damage to the walls of vessels (pale pink in color) neighboring the target vessel (300) (the largest black circle). FIG. 13(b) is an enlarged photograph of the target vessel (300) in region B of FIG. 13(a). The photograph more clearly exhibits a selective thermal response along the vessel wall (pale pink color).

Figure 14:
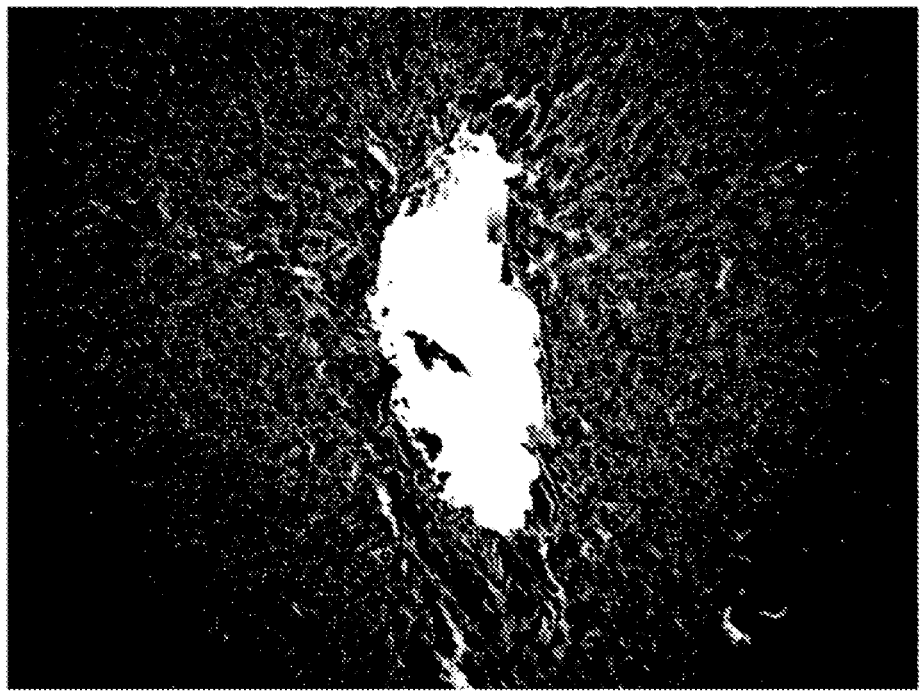
Figure 14:
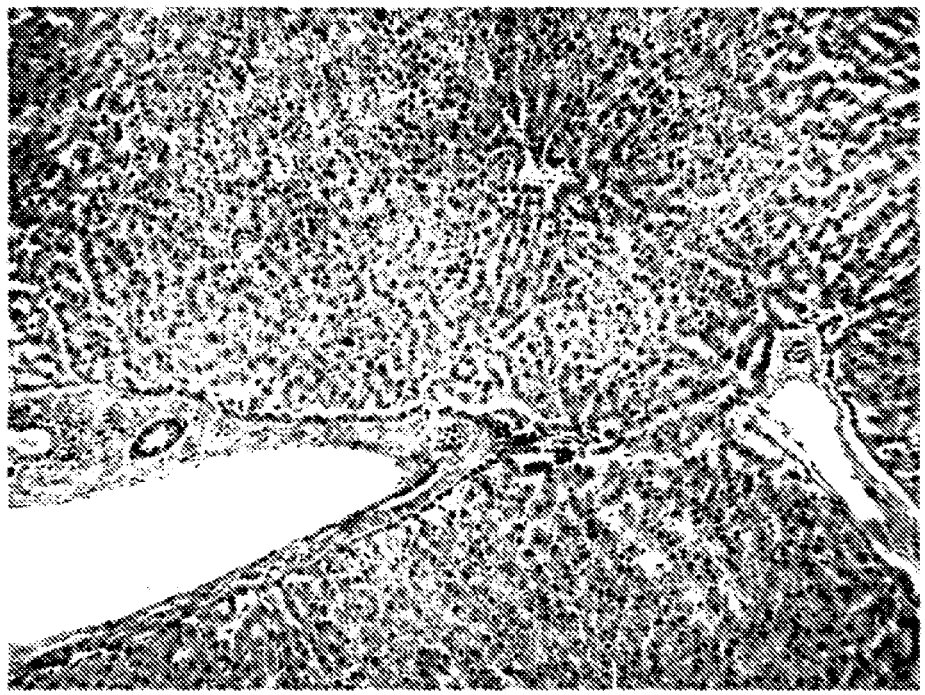
Figure 15:
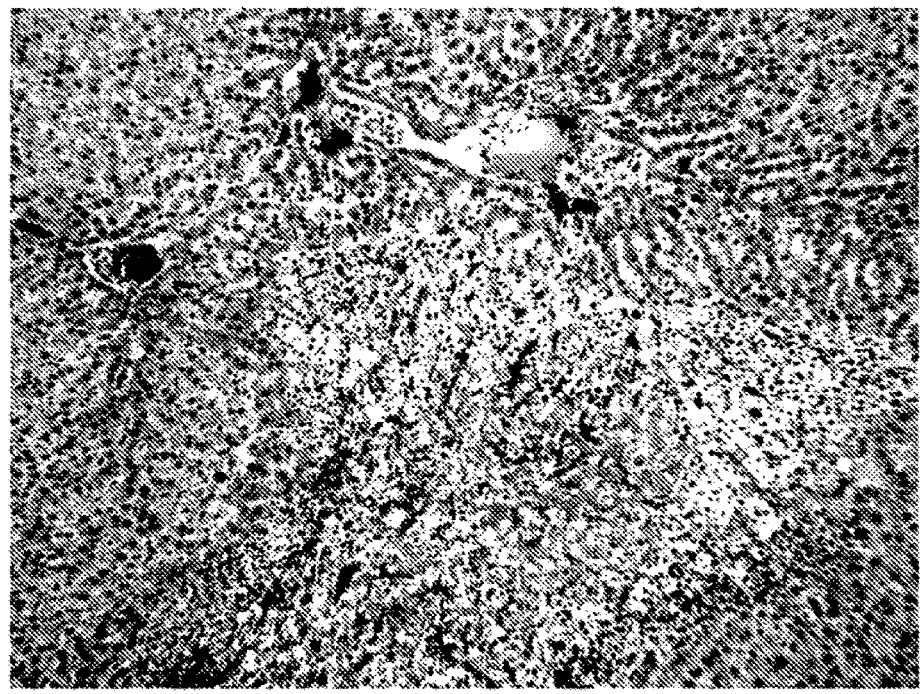

As shown in the figures, no thermal damage occurs in skin tissue between the two electrodes (153) in regions A (area around the electrodes), except for area surrounding the target vessel (300) in region B due to application of energy to electrodes (153) via system (100). FIGS. 14 and 15 shows experimental results from treating bovine liver tissue with the treatment system (100). Liver tissue was selected in order to more clearly show the selective thermal response on blood vessels, since liver tissue, in comparison with the skin, is composed primarily of hepatocytes and blood vessels and has relatively uniform tissue impedance, conductivity, and permittivity. Employing the system (100) to treat the liver tissue confirmed that the embodiments of the present invention may be employed to deliver electrical signal that selectively reacts with vessel in bovine tissue.

In addition, the electrical signal generated by system 100 mainly induced a thermal reaction along the outer surface of the vessel where the electrical signals were conducted along the vessel wall. Any tissue changes elicited by the thermal reaction induced by electrical signal were mainly observed in the tunica adventitia of blood vessel, while the tunica intima and tunica media were preserved. As stated above, non-selective aggressive destruction of vessels in a lesion may stimulate excessive production of Vascular Endothelial Growth Factor (VEGF) and promotes blood vessel regeneration by Vascular Hyperplasia, leading to worsening of the lesion. However, a selective thermal reaction, such as that induced by an embodiment of the present invention, along target vessel (300) or the outer layer of target vessel (300) may promote the regeneration of target vessel (300) in lesioned skin into normal vessel structure.

Moreover, inducing a selective thermal reaction may decrease the risk of side effects that may occur as the results of excessive nonselective damage to vascular and dermal structures and it improved clinically in melasma, dermal melasma, pigmentation, rosacea, flushing, or telangiectasia lesions.

In clinical experiments via the treatment system (100) for generating electrical signal with which to treat vessel in the skin, the treatment of melasma, dermal melasma, pigmentation, rosacea, flushing, or telangiectasia lesions, appropriate thermal damage to endothelial cell in vessel wall may restore abnormal vascular hyperplasia to normal, or normalizes the increased VEGF amount or levels, thereby promoting angiogenesis, and returning dilated vessel to normal size. Appropriate thermal damage to endothelial cells may also induce the phagocytosis or apoptosis thereof, enhancing the therapeutic effect vessel treatment.

Figure 19:
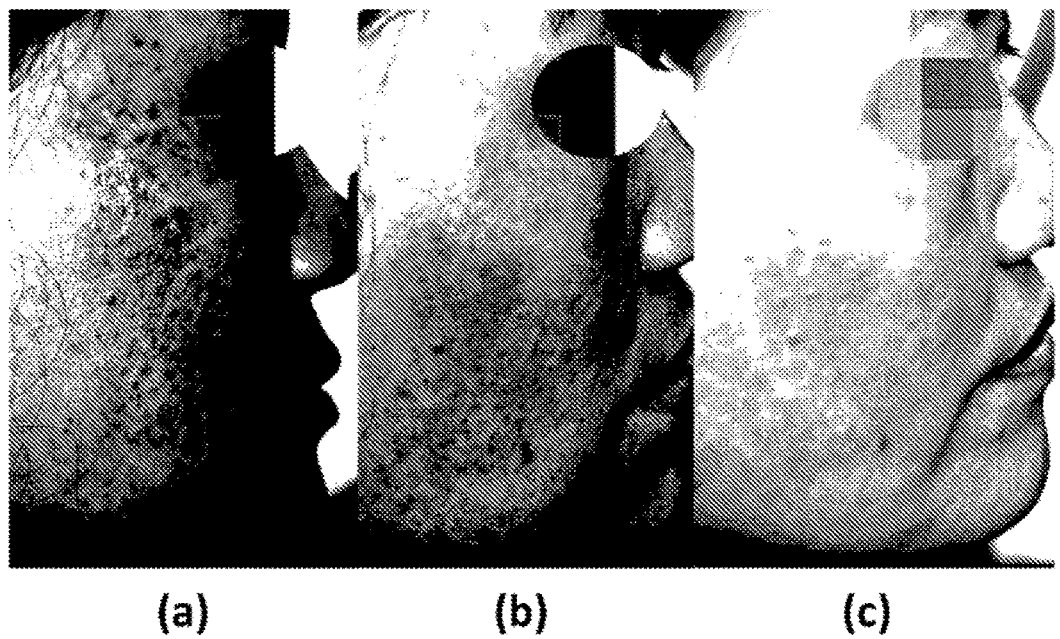
Figure 20:
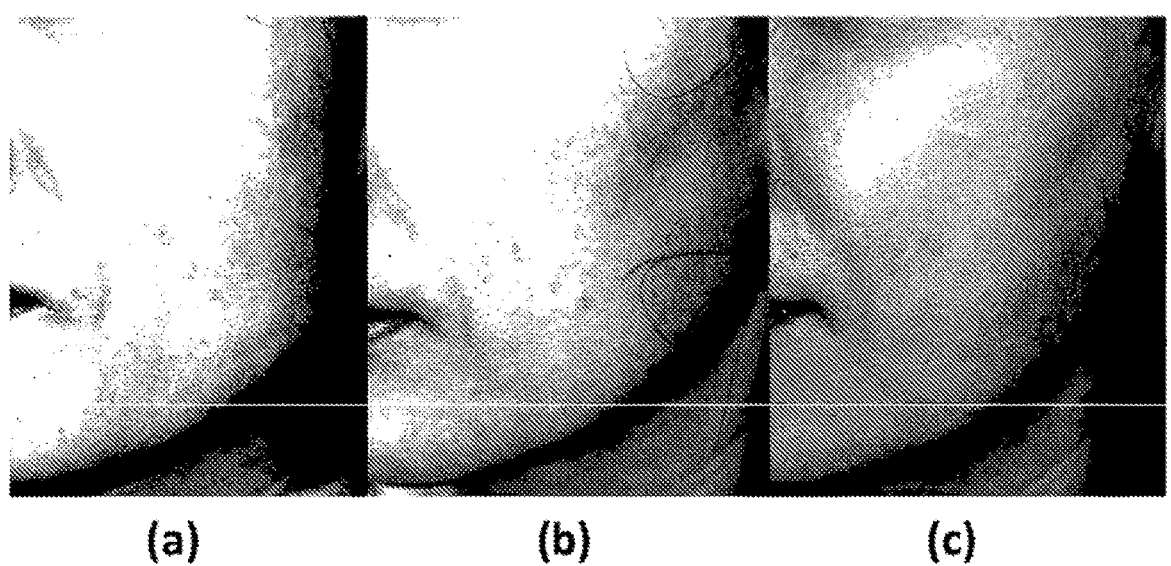

As shown in FIGS. 19 and 20, a vessel removed by the mechanism of inducing voluntary phagocytosis or apoptosis of endothelial cell show a markedly lower rate of recurrence, which was confirmed in clinical study. The technical principle of generating appropriate thermal damage to endothelial cell that constitute the causative, target vessel (300) that give rise to melasma, dermal melasma, pigmentation, rosacea, flushing, or telangiectasia lesions via an embodiment of the present invention will now be described in more detail.

Most of the blood in target vessels (300) that cause melasma, dermal melasma, pigmentation, rosacea, flushing, or telangiectasia is composed of water, accordingly the electrical conductivity of such a vessel in an electric field may be higher than that of surrounding tissue.

Thus, such a vessel strongly may attract most of the electrical current delivered to the skin in an embodiment. Also, vessel walls may exhibit much higher difference of impedance and permittivity from blood, and thus, in the presence of an electric field, the ionics that are located at the vessel wall may vibrate, causing a thermal reaction: electrical signal in the form of electromagnetic waves may cause water molecules and ionics to vibrate, thereby generating friction and heat.

Further, electric signals may exit vessels through blood that is in contact with the inner vessel wall, and heat may be dispersed by blood flowing through the vessel. Thus, a thermal reaction may be less likely to occur inside the vessel wall. Instead, heat may be concentrated on the outer vessel wall. If the conduction time of the electrical signal is further increased, more heat may be generated as a whole, although this can cause excessive damage to the blood vessel. Moreover, the heat generated in the vessel wall may cause heat damage to endothelial cell.

In accordance with the above, a treatment system (100) may be capable of eliciting a therapeutic thermal response concentrated on and around the vessel wall of causative, target vessels (300) that give rise to melasma, dermal melasma, pigmentation, rosacea, flushing, or telangiectasia lesions, without causing injury to surrounding tissue. Accordingly, by generating thermal damage to vessels in the skin with electrical signal, the treatment system (100) may induce selective thermal injury to endothelial cell of target vessel (300) and may generate frictional heat stemming from the vibration of water and ionic substances (or electrolytes) in target vessel (300). The treatment system (100) may be used for normalizing abnormal hyperplasia of endothelial cell or for normalizing increases in VEGF in treatment of conditions exhibiting angiogenesis or vasodilation. As is stated above, the treatment system (100) also may also induce phagocytosis or apoptosis of endothelial cell to achieve a desired therapeutic effect.

In order to induce phagocytosis or apoptosis of endothelial cell, an appropriate degree of thermal injury should be applied to endothelial cell. The results of repeated clinical experiments to find the optimal conditions for generating a sufficient thermal response using the treatment system (100) are shown in Table 1.

TABLE 1

|  | Condition 1 | Condition 2 | Condition 3 |
| --- | --- | --- | --- |
| Voltage (Vrms: 100Ω loaded) | 5-400 | 10-300 | 20-250 |
| Power (W: 100Ω loaded) | 0.25-1,600 | 1.0-900 | 4.0-625 |
| Conduction time (msec) | 1-500 | 5-400 | 10-300 |

The voltage and power values in Table 1 are measured values for when the treatment apparatus (100) is applied with a load resistance of 100Ω (Ohm; resistance). In other words, the voltage (Vrms unit: Volts) and power values are those at a load resistance of 100Ω (Ohm; resistance) for electrical signals delivered to electrodes (153) inserted in the skin (200) (epidermal layer and dermal layer [220]). The conduction time (msec unit: 0.001 sec) in Table 1 refers to the time over which electrical signal was applied to electrode (153) inserted into the skin (200). More specifically, the conduction time was measured as the time for delivering an electric signal to the skin (200) during one shot.

An embodiment of the system 100 may be employed with one or more of the parameter values shown in Table 1 via the user interface (180). The central processing unit (190) may then control the delivery of electrical signals according in the selected parameters. Using the treatment conditions in Table 1 in skin via system 100, melasma, dermal melasma, pigmentation, rosacea, flushing, or telangiectasia lesions were improved, but such conditions showed greater improvement when using the narrower treatment conditions in condition 2 in skin via system 100.

When the treatment conditions were set to condition 3 in system 100 and applied to skin, compared to condition 2, the degree of apoptosis and treatment effects on lesions were more prominent. Applying the parameters in conditions 2 to 3, the inventor of the present invention conducted clinical tests in humans and animals using the treatment apparatus (100) to treat melasma, dermal melasma, pigmentation, rosacea, flushing, and telangiectasia lesions. The results will now be described with reference to FIGS. 12 to 20.

FIG. 12 presents photographs of results from animal experiments on micro pig skin. Comparing results (a) before treatment and those (b) after treatment, vessel responses to electrical signal were visible in the dermis. There were no signs that the vessels were destroyed or that excessive bleeding occurred. Meanwhile, damage to vascular cells could be confirmed. FIGS. 14 and 15 are photographs of results from animal experiments on bovine liver tissue immediately after application of electrical signal via system 100.

Figure 16:
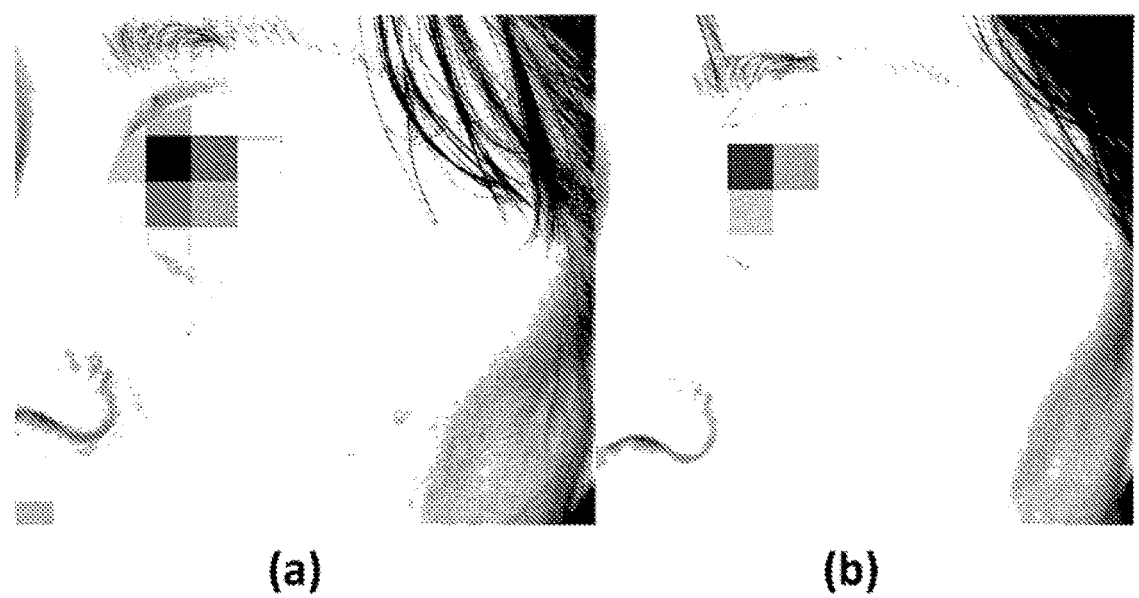

As seen in FIGS. 14 and 15, an electrical signal induced selective thermal reaction on vessels in the bovine liver tissue. The tissue changes elicited by the thermal reaction induced by electrical signals were mainly observed in the tunica adventitia of blood vessels, while the tunica intima and tunica media layers were preserved. FIG. 16 includes photographs of results from a clinical trial in human skin. Comparing results (a) before treatment and those (b) after 2 months of treatment via system 100 at 1-week intervals, marked improvement in vascular lesions, such as melasma, dermal melasma, pigmentation, rosacea, flushing, and telangiectasia, was noted.

Figure 17:
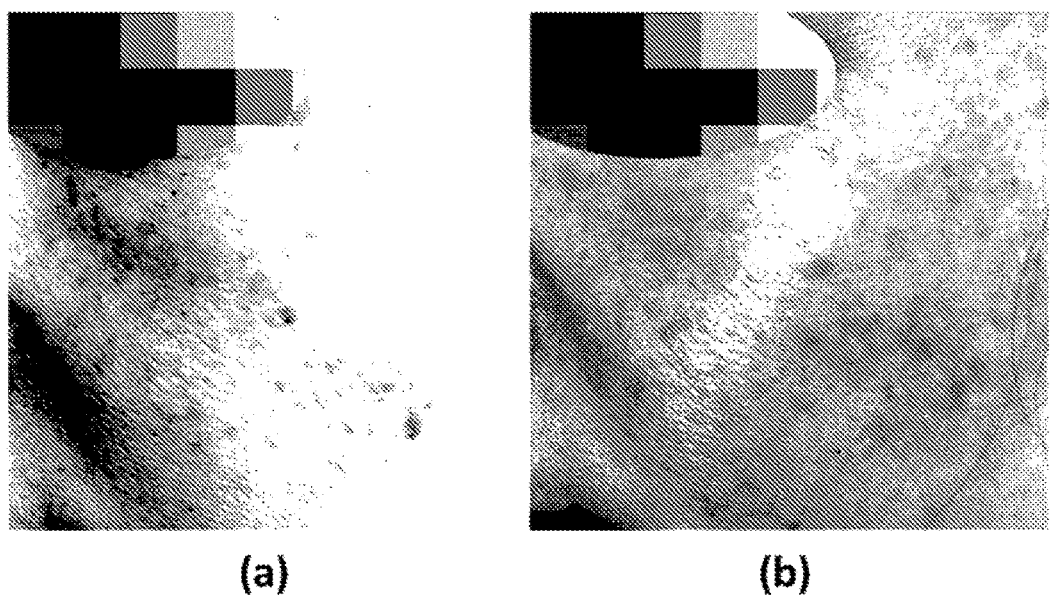
Figure 18:
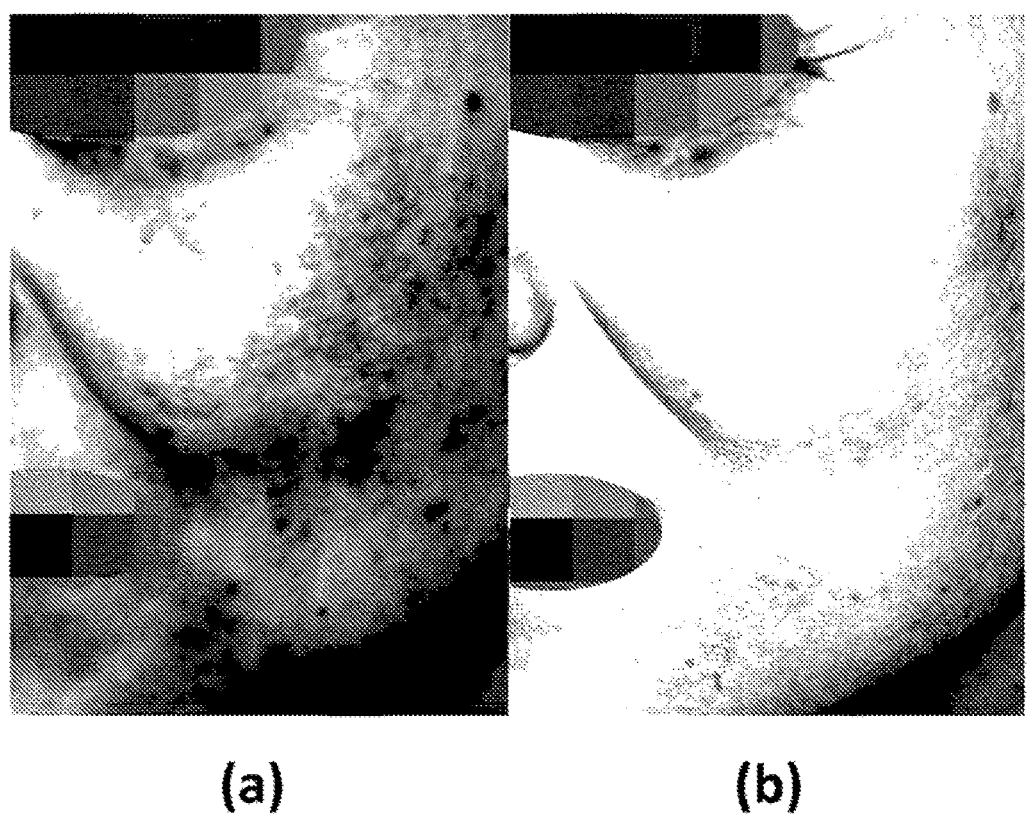

FIG. 17 includes photographs of results from another patient in the same clinical trial. Comparing results (a) before treatment and those (b) after 2 months of treatment using system 100 at 1-week intervals, marked improvement in vascular lesions, such as melasma, dermal melasma, pigmentation, rosacea, flushing, and telangiectasia, was noted. FIG. 18 includes photographs of results from a third patient included in the same clinical trial. Comparing results (a) before treatment and those (b) after 2 months of treatment via system 100 at 1-week intervals, marked improvement in vascular lesions, such as melasma, dermal melasma, pigmentation, rosacea, flushing, and telangiectasia, was noted.

FIG. 19 includes photographs of results from a fourth patient included in the same clinical trial. Comparing results (a) before treatment and those (b) after 2 months of treatment via system 100 at 1-week intervals with those (c) at 1 year after completing the treatment course, marked improvement in vascular lesions, such as melasma, dermal melasma, pigmentation, rosacea, flushing, and telangiectasia, was noted. Moreover, unlike conventional treatment, the appearance of the lesion continued to improve until one year after completion of the treatment, and there were no signs of lesion recurrence.

FIG. 20 includes photographs of results from a fifth patient included in the same clinical trial. Comparing results (a) before treatment and those (b) after 2 months of treatment via system 100 at 1-week intervals with those (c) at 1 year after completing the treatment course, marked improvement in vascular lesions, such as melasma, dermal melasma, pigmentation, rosacea, flushing, and telangiectasia, was noted. Moreover, unlike conventional treatment, the appearance of the lesion continued to improve until one year after completion of the treatment, and there were no signs of lesion recurrence.

In an embodiment, electro thermal responses induced by electrical signal applied to the skin via system 100 may vary according to the resistance of individual tissues. In an embodiment, electrical signals may be delivered to the skin in a monopolar mode via system 100, consisting of an active electrode with negative polarity and a ground electrode with positive polarity, or in a bipolar mode, in which both electrodes 153 are active. In the monopolar mode, an electrical circuit may be formed wherein electric current (electrons) flows from the active electrode through the patient's body to the ground electrode. In the bipolar mode, the flow of the electric current is limited to target tissues. In an embodiment, the bipolar mode may be preferable to the monopolar mode, because the transmission of energy in the bipolar mode may be safer to the human body and may be concentrated on target sites.

In an embodiment, the system 100 may transmit electric signals to the skin via electrode 153 that penetrate into target tissue, enabling it to more precisely control the depth of treatment, compared to conventional, non-invasive methods. Moreover, it may offer more uniform treatment at deeper regions of the skin. Another advantage of system 100 is that the discontinuous emission of energy may allow for a selective tissue thermal reaction to formed in the target tissue. Additionally, while systemic injury to blood vessels can be fatal, the invasive method of the system 100 according to an embodiment may facilitate localized treatment that is relatively safe.

In addition, further research with embodiments of the present invention has indicated that hair roots in the skin are conductors of electric current, particularly the outer sheath, the root muscle, and fibrous connective tissue, similar to the outer walls of vessels. Therefore, the treatment apparatus 100 may help improving hair loss, which is a complicated lesion. Additionally, by adjusting the intensity of electrical signal applied to the hair follicle via embodiments of the present invention permanent hair removal may be achieved. In treatment of melasma, embodiments of the present invention may be combined with conventional treatments, such as LASER toning, drug therapy, etc., in order to increase their therapeutic effects and to further lower the risk of recurrence.

In summary in an embodiment, thermal reactions may be selectively induced only on desired vessel tissue, and unnecessary damage to other surrounding tissues can be prevented or limited. In addition, by conducting electrical signal in a pulsed manner via an embodiment, it may be possible to avoid unnecessarily damaging surrounding tissue or causing excessive damage to vessel tissue, thereby potentially shortening the recovery period after treatment and reducing the risk of side effects. In addition, in an embodiment of the present invention, it may be possible to control the degree of thermal reaction generated on vessel tissue, thereby preventing or limiting bruising, vascular hyperplasia, and PIH, which are caused by excessive damage to blood vessels. Also, in contrast to currently available treatment, embodiments of the present invention utilize penetrating electrodes that allow for more uniform treatment of vascular tissue at deeper regions in the skin.

Further, with embodiments of the present invention, implementation of electrodes 153 in a bipolar configuration may confine the transmission of electrical current to within target lesions, unlike unipolar electrodes with which electrical current is applied to the whole body.

Such a configuration is particularly advantageous for treating patients suffering from heart disease or who wear a pacemaker, as they would be contraindicated for treatment with monopolar electrodes. Additionally, with embodiments of the present invention, vascular tissue may be selectively treated and pain caused by the thermal reaction can be reduced, providing a more comfortable procedure for the patient.

It is noted that embodiments of the present invention for use in treating blood vessel is not limited to only application in the dermatology applications. Embodiments of the present invention may also be applied to treat vessels in tissue of a patient, including Gastro Intestinal systems tissue including oral cavity, pharynx, larynx, esophagus, stomach, intestines, anus, liver, spleen, gall bladder, or pancreas, or Respiratory system tissue including trachea, lung, pleura, or chest wall, as well as brain, spinal cord, all neurological system and subcutaneous tissues.

The terminology used herein is for the purpose of describing particular embodiment only and is not intended to be limiting of the invention. The singular forms "a," "an," and "the" include plural referents unless the context clearly dictates otherwise. In the present application, the terms "comprises" or "having," etc. are intended to specify the presence of stated features, integers, steps, operations, elements, components, or combinations thereof, but do not preclude the presence or addition of one or more other features, integers, steps, operations, elements, components, or combinations thereof.

While the present invention has been shown and described with reference to exemplary embodiment thereof, it is to be understood that the invention is not limited to the disclosed exemplary embodiment, It will be understood by those skilled in the art that various changes in form and details may be made therein without departing from the spirit and scope of the present invention.

Embodiments of the present invention are recognized for its industrial applicability in the medical equipment industry.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. A method for treating a blood vessel in dermatological tissue, comprising:
    inserting at least two pins in the dermatological tissue so as to cause the blood vessel in dermatological tissue to be positioned between the at least two pins; and
    applying a repetitive pulsed electrical signal across the at least two pins to deliver electromagnetic energy to target the blood vessel,
    wherein the repetitive pulsed electrical signal has a plurality of pulses, each pulse having a duration, with consecutive pulses separated by a delay time,
    wherein the pulse duration is in a range of 10 to 300 msec, and the delay time is in a range of 5 to 100 msec.

2. The method of claim 1, wherein the duration of the delay time limits undesired thermal injury to the dermatological tissue surrounding the blood vessel caused by sustained delivery of electrical energy.

3. The method of claim 1, wherein the at least two pins form a bipolar configuration.

4. An apparatus for treating dermatological tissue, comprising:
    at least two pins configured to be inserted in the dermatological tissue and positioned to have a blood vessel in dermatological tissue therebetween; and
    an electrical signal generator electrically coupled to the at least two pins, and configured to create a repetitive pulsed electrical signal across the at least two pins to deliver electromagnetic energy to target the blood vessel,
    wherein the repetitive pulsed electrical signal has a plurality of pulses, each pulse having a duration, with consecutive pulses separated by a delay time,
    wherein the pulse duration is in a range of 10 to 300 msec, and the delay time is in a range of 5 to 100 msec.

5. The apparatus of claim 4, wherein the at least two pins form a bipolar configuration.

6. The apparatus of claim 4, wherein each pulse has a root mean square voltage level between 20 V and 250 V for a duration of 10 msec to 300 msec.

* * * * *